US012404347B2

(12) United States Patent
Kumar et al.

(10) Patent No.: US 12,404,347 B2
(45) Date of Patent: Sep. 2, 2025

(54) GLUCURONOXYLOMANNAN (GXM) RECEPTOR CHIMERIC ANTIGEN RECEPTORS AND USE THEREOF

(71) Applicant: Board of Regents, The University of Texas System, Austin, TX (US)

(72) Inventors: Pappanaicken Kumar, Houston, TX (US); Thiago Aparecido Da Silva, Houston, TX (US); Paul J. Hauser, Houston, TX (US)

(73) Assignee: BOARD OF REGENTS, THE UNIVERSITY OF TEXAS SYSTEM, Austin, TX (US)

( * ) Notice: Subject to any disclaimer, the term of this patent is extended or adjusted under 35 U.S.C. 154(b) by 970 days.

(21) Appl. No.: 17/429,090

(22) PCT Filed: Feb. 7, 2020

(86) PCT No.: PCT/US2020/017156
§ 371 (c)(1),
(2) Date: Aug. 6, 2021

(87) PCT Pub. No.: WO2020/163682
PCT Pub. Date: Aug. 13, 2020

(65) Prior Publication Data
US 2022/0106407 A1    Apr. 7, 2022

Related U.S. Application Data

(60) Provisional application No. 62/802,532, filed on Feb. 7, 2019.

(51) Int. Cl.
| | |
|---|---|
| *C07K 16/44* | (2006.01) |
| *A61K 40/11* | (2025.01) |
| *A61K 40/31* | (2025.01) |
| *A61K 40/44* | (2025.01) |
| *A61K 45/06* | (2006.01) |
| *A61P 31/10* | (2006.01) |
| *C07K 14/705* | (2006.01) |
| *C07K 14/725* | (2006.01) |
| *C12N 5/0783* | (2010.01) |

(52) U.S. Cl.
CPC .............. *C07K 16/44* (2013.01); *A61K 40/11* (2025.01); *A61K 40/31* (2025.01); *A61K 40/44* (2025.01); *A61K 45/06* (2013.01); *A61P 31/10* (2018.01); *C07K 14/7051* (2013.01); *C07K 14/70521* (2013.01); *C12N 5/0636* (2013.01); *A61K 2239/17* (2023.05); *A61K 2239/31* (2023.05); *A61K 2239/38* (2023.05); *C07K 2317/622* (2013.01); *C07K 2319/02* (2013.01); *C07K 2319/03* (2013.01)

(58) Field of Classification Search
None
See application file for complete search history.

(56) References Cited

U.S. PATENT DOCUMENTS

| | | |
|---|---|---|
| 5,807,559 A | 9/1998 | Jondal |
| 2012/0263719 A1 | 10/2012 | Mirelman et al. |
| 2015/0018532 A1 | 1/2015 | Thornton |
| 2017/0066838 A1 | 3/2017 | Puléet al. |
| 2017/0158749 A1 | 6/2017 | Cooper et al. |
| 2017/0224798 A1 | 8/2017 | Cooper et al. |
| 2018/0265595 A1 | 9/2018 | Cooper et al. |
| 2018/0298068 A1 | 10/2018 | Albelda |

OTHER PUBLICATIONS

Casadevall, et. al., Antimicrobial Agents and Chemotherapy, 1998, 42, 1437-1446 (Year: 1998).*
Curran, et. al., J Gene Med, 2012, 14, 405-415 (Year: 2012).*
Sadelain, et. al., Cancer Discov. 2013, 3, 388-398 (Year: 2013).*
Kumaresan, et. al., PNAS, 2014, 111, 10660-10665 (Year: 2014).*
Rudikoff, et. al., PNAS, 1982, 79, 1979-1982 (Year: 1982).*
Janeway, et. al., Immunobiology: The Immune System in Health and Disease, 5th edition, 2001 (Year: 2001).*
López-Medrano, R. et al., "*Aspergillus fumigatus* antigens," *Microbiology*, 141 (1995): 2699-2704.
Casadevall, A. et al., "Characterization of a Murine Monoclonal Antibody to *Cryptococcus neoformans* Polysaccharide That Is a Candidate for Human Therapeutic Studies," *Antimicrobial Agents and Chemotherapy*, 42.6 (1998):1437-1446.
Kumaresan, P. R. et al., "Bioengineering T cells to target carbohydrate to treat opportunistic fungal infection," *Proc Natl Acad Sci U S A*, 111.29 (2014):10660-10665.
Kumaresan, P. R. et al., "Methods for Controlling Invasive Fungal Infections Using CD8+ $^{T\ Cells}$," *Frontiers in Immunology*, 8 (2018): 1-14.
Liu, T. et al., "Glucuronoxylomannan promotes the generation of antigen-specific T regulatory cell that suppresses the antigen-specific Th2 response upon activation," *J. Cell. Mol. Med.*, 13.8B (2009): 1765-1774.
McLean, G. R. et al. "Isotype can affect the fine specificity of an antibody for a polysaccharide antigen," *The Journal of Immunology*, 169.3 (2002): 1379-1386.
PCT International Search Report and Written Opinion issued for International Patent Application No. PCT/US2020/017156, dated Apr. 29, 2020.
PCT International Preliminary Report on Patentability issued for International Patent Application No. PCT/US2020/017156, dated Aug. 19, 2021.

(Continued)

*Primary Examiner* — Misook Yu
*Assistant Examiner* — Samantha Lake Hopkins
(74) *Attorney, Agent, or Firm* — Parker Highlander PLLC

(57) ABSTRACT

Provided herein are chimeric antigen receptors (CARs) comprising a glucuronoxylomannan receptor antigen-binding domain. Further provided herein are immune cells expressing the GXMR-CARs as well as methods of their use in the treatment of cryptococcosis.

13 Claims, 19 Drawing Sheets

Specification includes a Sequence Listing.

(56) References Cited

OTHER PUBLICATIONS

Saijo, S. et al., "Dectin-2 Recognition of a-Mannans and Induction of Th17 Cell Differentiation Is Essential for Host Defense against Candida albicans," *Immunity*, 32 (2010): 681-691.

Zhong, Z. et al., "Antifungal Activity of a Human Antiglucuronoxylomannan Antibody," *Clinical and Diagnostic Laboratory Immunology*, 5.1 (1998): 58-64.

Mikulska, M. et al. "The use of mannan antigen and anti-mannan antibodies in invasive candidiasis: recommendations from the Third European Conference on in Leukemia," *Critical Care*, 14 (2010): 1-14.

* cited by examiner

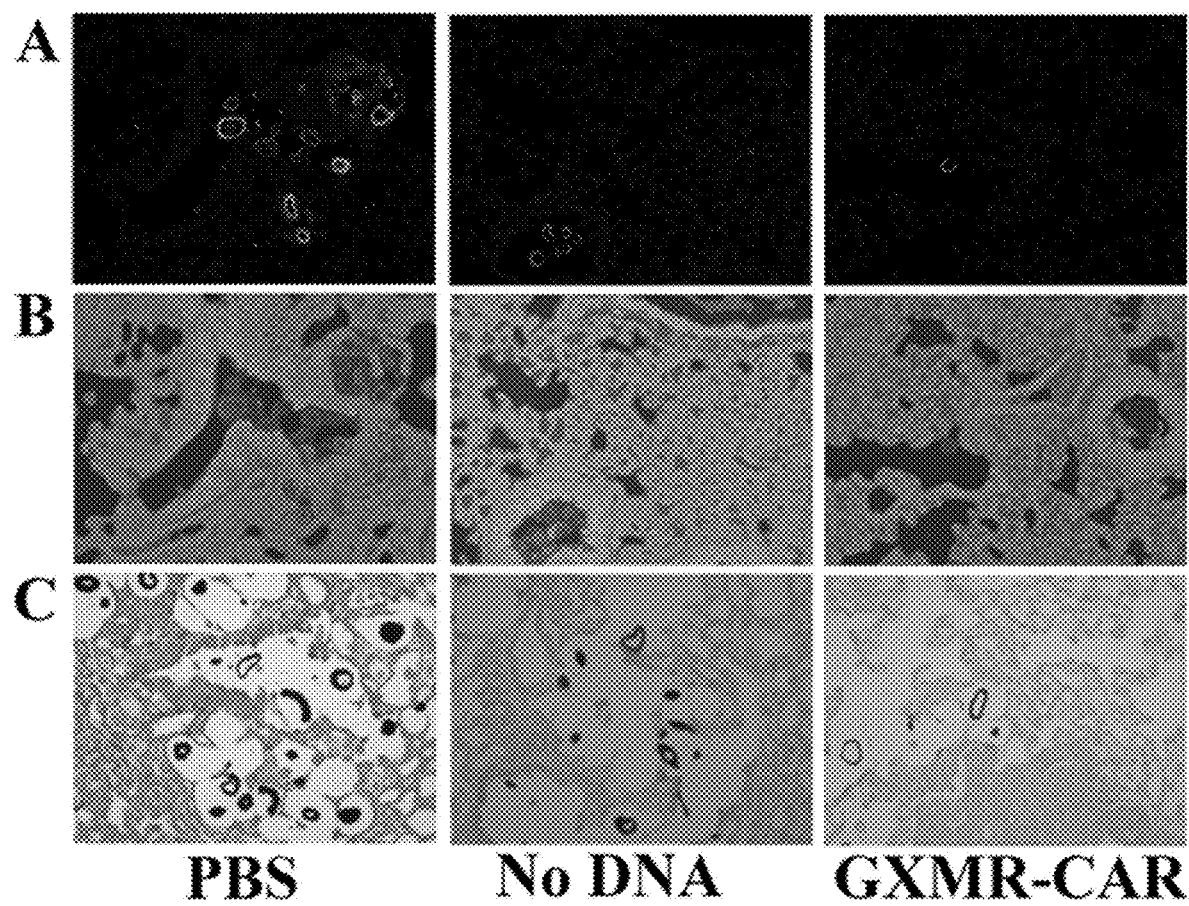
FIG. 12A-C

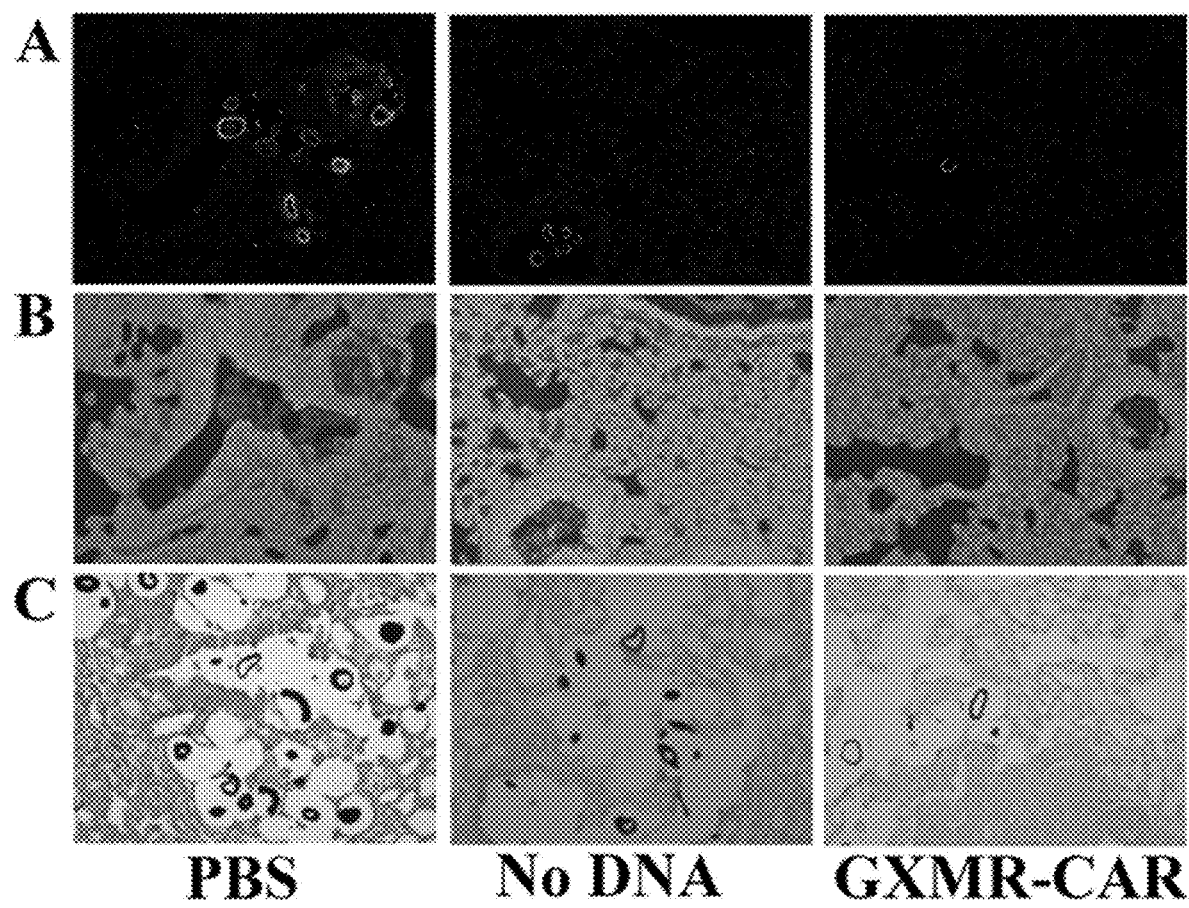
FIG. 12A-C

SEQUENCE LISTING

```
<160> NUMBER OF SEQ ID NOS: 12

<210> SEQ ID NO 1
<211> LENGTH: 750
<212> TYPE: DNA
<213> ORGANISM: Artificial sequence
<220> FEATURE:
<223> OTHER INFORMATION: Synthetic oligonucleotide

<400> SEQUENCE: 1
gtggttatga cccagacacc tctgagcctg cctgtgtctg ctggcgatca ggccagcatc      60
agctgtagaa gctctcagag cctggtgcac agcaacggca atacctacct gcactggtat     120
ctgcagaagc ccggccagtc tcctaagctg ctgatctaca aggtgtccaa cagattcagc     180
ggcgtgcccg ataagtttag cggctctggc agcggcaccg acttcaccct gaagatctct     240
agagtggaag ccgaggacct gggcgtgtac ttctgtagcc agtctaccca cgtgccatgg     300
acctttggcg gcggaacaaa gctggaaatc aagggctcta ccagcggcag cggaaagcct     360
ggatctggcg aaggatctac caagggcgac gtgaagctgg tggaatctgg cggaggactg     420
gttaagctcg gcggctctct gaaactgtct tgcgtggcca gcggcttcac ctgtagcagc     480
tacttcatga gctgggtccg acagaccoct gagaagagac tggaactggt ggccatgatc     540
aacaacaacg gcgacaagac ctactatccc gacaccgtga agggcagatt caccatcagc     600
cgggacaacg ccaagaacac cctgtacctg cagatgagca gcctgaagtc cgaggacacc     660
gccatgtact actgcgccag aagagatggc accttcggca accacttcga ttactggggc     720
cagggcacca cactgacagt tagctctagc                                      750

<210> SEQ ID NO 2
<211> LENGTH: 250
<212> TYPE: PRT
<213> ORGANISM: Artificial sequence
<220> FEATURE:
<223> OTHER INFORMATION: Synthetic amino acid

<400> SEQUENCE: 2

Val Val Met Thr Gln Thr Pro Leu Ser Leu Pro Val Ser Ala Gly Asp
1               5                   10                  15

Gln Ala Ser Ile Ser Cys Arg Ser Ser Gln Ser Leu Val His Ser Asn
                20                  25                  30

Gly Asn Thr Tyr Leu His Trp Tyr Leu Gln Lys Pro Gly Gln Ser Pro
            35                  40                  45

Lys Leu Leu Ile Tyr Lys Val Ser Asn Arg Phe Ser Gly Val Pro Asp
        50                  55                  60

Lys Phe Ser Gly Ser Gly Ser Gly Thr Asp Phe Thr Leu Lys Ile Ser
65                  70                  75                  80

Arg Val Glu Ala Glu Asp Leu Gly Val Tyr Phe Cys Ser Gln Ser Thr
```

|   |   |   | 85 |   |   |   | 90 |   |   |   | 95 |   |   |
|---|---|---|---|---|---|---|---|---|---|---|---|---|---|
| His | Val | Pro | Trp | Thr | Phe | Gly | Gly | Gly | Thr | Lys | Leu | Glu | Ile | Lys | Gly |
|   |   |   |   | 100 |   |   |   |   | 105 |   |   |   |   | 110 |   |

Ser Thr Ser Gly Ser Gly Lys Pro Gly Ser Gly Glu Gly Ser Thr Lys
            115                 120                 125

Gly Asp Val Lys Leu Val Glu Ser Gly Gly Gly Leu Val Lys Leu Gly
        130                 135                 140

Gly Ser Leu Lys Leu Ser Cys Val Ala Ser Gly Phe Thr Cys Ser Ser
145                 150                 155                 160

Tyr Phe Met Ser Trp Val Arg Gln Thr Pro Glu Lys Arg Leu Glu Leu
                165                 170                 175

Val Ala Met Ile Asn Asn Asn Gly Asp Lys Thr Tyr Tyr Pro Asp Thr
            180                 185                 190

Val Lys Gly Arg Phe Thr Ile Ser Arg Asp Asn Ala Lys Asn Thr Leu
        195                 200                 205

Tyr Leu Gln Met Ser Ser Leu Lys Ser Glu Asp Thr Ala Met Tyr Tyr
    210                 215                 220

Cys Ala Arg Arg Asp Gly Thr Phe Gly Asn His Phe Asp Tyr Trp Gly
225                 230                 235                 240

Gln Gly Thr Thr Leu Thr Val Ser Ser Ser
                245                 250

```
<210> SEQ ID NO 3
<211> LENGTH: 3498
<212> TYPE: DNA
<213> ORGANISM: Artificial sequence
<220> FEATURE:
<223> OTHER INFORMATION: Synthetic oligonucleotide

<400> SEQUENCE: 3
atgctgctgc tggtgaccag cctgctgctg tgtgagctgc ccacccccgc ctttctggat      60
gtggtgatga cccagacccc gctgagcctg ccggtgagcg cggcgatca ggcgagcatt     120
agctgccgca gcagccagag cctggtgcat agcaacggca cacctatct gcattggtat     180
ctgcagaaac cgggccagag cccgaaactg ctgatttata agtgagcaa ccgctttagc     240
ggcgtgccgg ataaatttag cggcagcggc agcggcaccg attttaccct gaaaattagc     300
cgcgtggaag cggaagatct ggcgtgtat ttttgcagcc agagcaccca tgtgccgtgg     360
acctttggcg gcggcaccaa actggaaatt aaaggcagca cctccggcag cggcaagcct     420
ggcagcggcg agggcagcac caagggcgat gtgaaactgg tggaaagcgg cggcggcctg     480
gtgaaactgg gcggcagcct gaaactgagc tgcgtggcga gcggctttac ctgcagcagc     540
tattttatga gctgggtgcg ccagaccccg aaaaacgcc tggaactggt ggcgatgatt     600
aacaacaacg gcgataaaac ctattatccg gataccgtga aaggccgctt taccattagc     660
cgcgataacg cgaaaaacac cctgtatctg cagatgagca gcctgaaaag cgaagatacc     720
gcgatgtatt attgcgcgcg ccgcgatggc acctttggca accattttga ttattggggc     780
cagggcacca ccctgaccgt gagcagcagc gtggagagca agtacggccc tcctgccc      840
ccttgccctg ccccgagtt cgaggcgga cccagcgtgt tcctgttccc ccccaagccc     900
aaggacaccc tgatgatcag ccggacccc gaggtgacct gtgtggtggt ggacgtgtcc     960
caggaggacc ccgaggtcca gttcaactgg tacgtggacg gcgtggaggt gcacaacgcc    1020
aagaccaagc ccgggagga gcagttccag agcacctacc gggtggtgtc cgtgctgacc    1080
gtgctgcacc aggactggct gaacggcaag gaatacaagt gtaaggtgtc caacaagggc    1140
```

```
ctgcccagca gcatcgagaa aaccatcagc aaggccaagg gccagcctcg ggagccccag    1200
gtgtacaccc tgcccctag ccaagaggag atgaccaaga atcaggtgtc cctgacctgc     1260
ctggtgaagg gcttctaccc cagcgacatc gccgtggagt gggagagcaa cggccagccc    1320
gagaacaact acaagaccac cccccctgtg ctggacagcg acggcagctt cttcctgtac    1380
agcaggctga ccgtggacaa gagccggtgg caggagggca cgtctttag ctgctccgtg     1440 atgcacgata ggagcaagcg gagcagaggc ggccacagcg actacatgaa catgaccccc    1500
cggaggcctg cccccacccg gaagcactac cagccctacg cccctcccag ggacttcgcc    1560
gcctaccgga gcgggtgaa gttcagccgga gcgccgacg cccctgccta ccagcagggc    1620
cagaaccagc tgtacaacga gctgaacctg gccggaggg aggagtacga cgtgctggac     1680
aagcggagag gccgggaccc tgagatgggc ggcaagcccc ggagaaagaa ccctcaggag    1740
ggcctgtata cgaactgca gaaagacaag atggccgagg cctacagcga gatcggcatg    1800
aagggcgagc ggcggagggg caagggccac gacggcctgt accagggcct gagcaccgcc    1860
accaaggata cctacgacgc cctgcacatg caggccctgc ccccagagc tagcggcagt     1920 ggagagggca gaggaagtct gctaacatgc ggtgacgtcg aggagaatcc tggcccagtg    1980
agcaagggcg aggagctgtt caccggggtg gtgcccatcc tggtcgagct ggacggcgac    2040
gtaaacggcc acaagttcag cgtgtccggc gagggcgagg gcgatgccac ctacggcaag    2100
ctgaccctga agttcatctg caccaccggc aagctgcccg tgccctggcc caccctcgtg    2160
accaccctga cctacggcgt gcagtgcttc agccgctacc ccgaccacat gaagcagcac    2220
gacttcttca gtccgccat gcccgaaggc tacgtccagg agcgcaccat cttcttcaag     2280
gacgacggca actacaagac ccgcgccgag gtgaagttcg agggcgacac cctggtgaac    2340
cgcatcgagc tgaagggcat cgacttcaag gaggacggca acatcctggg gcacaagctg    2400
gagtacaact acaacagcca caacgtctat atcatggccg acaagcagaa gaacggcatc    2460
aaggtgaact tcaagatccg ccacaacatc gaggacggca gcgtgcagct cgccgaccac    2520
taccagcaga acacccccat cggcgacggc cccgtgctgc tgcccgacaa ccactacctg    2580
agcacccagt ccgccctgag caaagacccc aacgagaagc gcgatcacat ggtcctgctg    2640
gagttcgtga ccgccgccgg gatcactctc ggcatggacg agctgtacaa gtaagaattc    2700
gatatcaagc ttatcgataa tcaacctctg gattacaaaa tttgtgaaag attgactggt    2760
attcttaact atgttgctcc ttttacgcta tgtggatacg ctgctttaat gcctttgtat    2820
catgctattg cttcccgtat ggctttcatt ttctcctcct tgtataaatc ctggttgctg    2880
tctctttatg aggagttgtg gcccgttgtc aggcaacgtg gcgtggtgtg cactgtgttt    2940
gctgacgcaa ccccactggt tggggcatt gccaccacct gtcagctcct ttccgggact    3000
ttcgctttcc cctccctat gccacggcg gaactcatcg ccgcctgcct tgcccgctgc     3060
tggacagggg ctcggctgtt gggcactgac aattccgtgg tgttgtcggg gaaatcatcg    3120
tcctttcctt ggctgctcgc ctgtgttgcc acctggattc tgcgcgggac gtccttctgc    3180
tacgtccctt cggccctcaa tccagcggac cttccttccc gcggcctgct gccggctctg    3240
cggcctcttc cgcgtcttcg ccttcgccct cagacgagtc ggatctccct ttgggccgcc    3300
tccccgcatc gataccgtcg acctcgagac ctagaaaaac atggagcaat cacaagtagc    3360
aatacagcag ctaccaatgc tgattgtgcc tggctagaag cacaagagga ggaggaggtg    3420
ggttttccag tcacacctca ggtaccttta agaccaatga cttacaaggc agctgtagat    3480
```

-continued cttagccact tttaaaa                                                3498

<210> SEQ ID NO 4
<211> LENGTH: 56
<212> TYPE: DNA
<213> ORGANISM: Artificial sequence
<220> FEATURE:
<223> OTHER INFORMATION: Synthetic oligonucleotide

<400> SEQUENCE: 4
caccggcgaa ggaggcctat catgaagatc tatcgattgt acagctagcc gccacc      56

<210> SEQ ID NO 5
<211> LENGTH: 56
<212> TYPE: DNA
<213> ORGANISM: Artificial sequence
<220> FEATURE:
<223> OTHER INFORMATION: Synthetic oligonucleotide

<400> SEQUENCE: 5
caccggcgaa ggaggcctat catgaagatc tatcgattgt acagctagcc gccacc      56

<210> SEQ ID NO 6
<211> LENGTH: 690
<212> TYPE: DNA
<213> ORGANISM: Artificial sequence
<220> FEATURE:
<223> OTHER INFORMATION: Synthetic oligonucleotide

<400> SEQUENCE: 6
gagagcaagt acggccctcc ctgccccct tgccctgccc ccgagttcga gggcggaccc     60
agcgtgttcc tgttcccccc caagcccaag acaccctga tgatcagccg gaccccgag    120 gtgacctgtg tggtggtgga cgtgtcccag gaggaccccg aggtccagtt caactggtac   180
gtggacggcg tggaggtgca acgccaag accaagcccc gggaggagca gttccagagc    240
acctaccggg tggtgtccgt gctgaccgtg ctgcaccagg actggctgaa cggcaaggaa   300
tacaagtgta aggtgtccaa caagggcctg ccagcagca tcgagaaaac catcagcaag   360
gccaagggcc agcctcggga gccccaggtg tacaccctgc ccctagcca agaggagatg    420 accaagaatc aggtgtccct gacctgcctg gtgaagggct tctaccccag cgacatcgcc   480
gtggagtggg agagcaacgg ccagcccgag aacaactaca agaccacccc cctgtgctg    540 gacagcgacg gcagcttctt cctgtacagc aggctgaccg tggacaagag ccggtggcag   600
gagggcaacg tctttagctg ctccgtgatg cacgaggccc tgcacaacca ctacacccag   660
aagagcctgt ccctgagcct gggcaagatg                                    690

<210> SEQ ID NO 7
<211> LENGTH: 81
<212> TYPE: DNA
<213> ORGANISM: Artificial sequence
<220> FEATURE:
<223> OTHER INFORMATION: Synthetic oligonucleotide

<400> SEQUENCE: 7
ttctgggtgc tggtcgtggt gggtggcgtg ctggcctgct acagcctgct ggtgacagtg     60
gccttcatca tctttttgggt g                                            81

<210> SEQ ID NO 8
<211> LENGTH: 123
<212> TYPE: DNA
<213> ORGANISM: Artificial sequence

```
<220> FEATURE:
<223> OTHER INFORMATION: Synthetic oligonucleotide

<400> SEQUENCE: 8
aggagcaagc ggagcagagg cggccacagc gactacatga acatgacccc ccggaggcct      60
ggccccaccc ggaagcacta ccagccctac gcccctccca gggacttcgc cgcctaccgg     120
agc                                                                  123

<210> SEQ ID NO 9
<211> LENGTH: 339
<212> TYPE: DNA
<213> ORGANISM: Artificial sequence
<220> FEATURE:
<223> OTHER INFORMATION: Synthetic oligonucleotide

<400> SEQUENCE: 9
cgggtgaagt tcagccggag cgccgacgcc cctgcctacc agcagggcca gaaccagctg      60
tacaacgagc tgaacctggg ccggagggag gagtacgacg tgctggacaa gcggagaggc     120
cgggaccctg agatgggcgg caagccccgg agaaagaacc ctcaggaggg cctgtataac     180
gaactgcaga agacaagat ggccgaggcc tacagcgaga tcggcatgaa gggcgagcgg     240
cggaggggca agggccacga cggcctgtac cagggcctga gcaccgccac caaggatacc     300
tacgacgccc tgcacatgca ggccctgccc cccagatga                           339

<210> SEQ ID NO 10
<211> LENGTH: 16
<212> TYPE: DNA
<213> ORGANISM: Artificial sequence
<220> FEATURE:
<223> OTHER INFORMATION: Synthetic primer

<400> SEQUENCE: 10
gccgcgacct gcaaag                                                    16

<210> SEQ ID NO 11
<211> LENGTH: 25
<212> TYPE: DNA
<213> ORGANISM: Artificial sequence
<220> FEATURE:
<223> OTHER INFORMATION: Synthetic primer

<400> SEQUENCE: 11
ggtaatcacc ttcccactaa cacat                                          25

<210> SEQ ID NO 12
<211> LENGTH: 13
<212> TYPE: DNA
<213> ORGANISM: Artificial sequence
<220> FEATURE:
<223> OTHER INFORMATION: Synthetic primer

<400> SEQUENCE: 12
acgtcggctc gcc                                                       13
```

GLUCURONOXYLOMANNAN (GXM) RECEPTOR CHIMERIC ANTIGEN RECEPTORS AND USE THEREOF

CROSS-REFERENCE TO RELATED APPLICATIONS

This application is a national phase application under 35 U.S.C. § 371 of International Application No. PCT/US2020/017156, filed Feb. 7, 2020, which claims the benefit of U.S. Provisional Patent Application No. 62/802,532, filed Feb. 7, 2019, each of which is incorporated herein by reference in its entirety.

INCORPORATION OF SEQUENCE LISTING

The sequence listing that is contained in the file named "UTFCP1375WO_ST25.txt", which is 12,000 Bytes (as measured in Microsoft Windows®) and was created on Feb. 5, 2020, is filed herewith by electronic submission and is incorporated by reference herein.

BACKGROUND

1. Field

The present invention relates generally to the fields of immunology and molecular biology. More particularly, it concerns anti-fungal chimeric antigen receptors (CARs).

2. Description of Related Art

Despite appropriate antifungal treatment, the management of cryptococcal disease remains challenging, especially in immunocompromised patients, such as human immunodeficiency virus (HIV)-infected individuals and solid organ transplant recipients. 6-8% of the late stage HIV patients get *Cryptococcus neoformans* infection. In spite of available anti-fungal drugs, invasive fungal infections (IFI) are associated with high mortality rates worldwide, causing an estimated 1 million deaths each year, a number comparable to tuberculosis. *Candida, Aspergillus, Cryptococcus* and *pneumocystis* account for 90% of the deaths caused by IFI. Glucuronoxylomannan (GXM) is a major polysaccharide of *C. neoformans* capsule that gives protection against phagocytes activity. Many currently available drugs face limitations, such as drug resistance, harmful side effects, and negative interactions with other drugs. So far, no curative therapy is available to treat drug resistant IFI.

SUMMARY

In certain embodiments, there is provided a chimeric antigen receptor (CAR) comprising a glucuronoxylomannan (GXM) antigen-binding domain.

In certain aspects, the GXM antigen-binding domain is selected from the group consisting of F(ab')2, Fab', Fab, Fv, and scFv. In some aspects, the GXM antigen-binding domain is a scFv. In certain aspects, the GXM scFv comprises an amino acid sequence with at least 80% (e.g., at least about 81%, 82%, 83%, 84%, 85%, 86%, 87%, 88%, 89%, 90%, 91%, 92%, 93%, 94%, 95%, 96%, 97%, 98%, or 99%) sequence identity to SEQ ID NO:2. In particular aspects, the GXMR scFv comprises an amino acid sequence of SEQ ID NO:2. In some aspects, the GXMR scFv is encoded by a nucleotide sequence with at least 80% (e.g., at least about 81%, 82%, 83%, 84%, 85%, 86%, 87%, 88%, 89%, 90%, 91%, 92%, 93%, 94%, 95%, 96%, 97%, 98%, or 99%) sequence identity to SEQ ID NO:1. In some aspects, GXMR scFv is encoded by a nucleotide sequence of SEQ ID NO:1.

In some aspects, the CAR comprises signaling domains CD3ξ, CD28, OX40/CD134, 4-1BB/CD137, TRAM, MyD88, TRAF 6, Toll-like-receptor (TLR) family members or a combination thereof. In certain aspects, the CAR comprises signaling domains CD28 and CD32. In particular aspects, the CAR comprises a CD28, CD8α, CD134, CD137, pattern recognition receptor (PRR) or TLR transmembrane domain. In some aspects, the CAR comprises a CD28 transmembrane domain. In some aspects, the CAR comprises an IgG4-M spacer. In certain aspects, the CAR comprises the GXM scFv, IgG4-M spacer, CD28 transmembrane domain, CD28 signaling domain, and CD3 signaling domain. In particular aspects, the CAR comprises a nucleotide sequence with at least 80% (e.g., at least about 81%, 82%, 83%, 84%, 85%, 86%, 87%, 88%, 89%, 90%, 91%, 92%, 93%, 94%, 95%, 96%, 97%, 98%, or 99%) sequence identity to SEQ ID NO:3. In specific aspects, the CAR comprises a nucleotide sequence of SEQ ID NO:3.

Further provided herein is an isolated polynucleotide encoding a CAR of the embodiments (e.g., a CAR comprising a GXM antigen-binding domain). In some aspects, the polynucleotide comprises SEQ ID NO:3. Also provided herein is an expression vector, such as a plasmid, encoding a CAR of the embodiments. In some aspects, the vector is further defined as a viral vector, such a lentiviral vector or retroviral vector.

In another embodiment, there is provided a host cell engineered to express a CAR comprising a GXM antigen-binding domain according to the embodiments. In some aspects, the host cell is further defined as an immune cell. In certain aspects, the immune cell is a T cell, lymphocyte, myelocyte, NK cell, NKT cell, macrophage, or dendritic cell. For example, the T cell is a αβ T cell, a γδ T cell, a CD4, CD8, regulatory, T17, follicular helper (Tfh), Th1, or Th2 T cell. In some aspects, the immune cell is derived from peripheral blood monocytes (PBMCs), or tumor microenvironment. In certain aspects, the immune cell is a Jurkat cell, NK-92 cell, KHYG-1 cell, or U937 cell. The immune cell may be allogeneic or autologous. In some aspects, the immune cell is isolated from peripheral blood, cord blood, or bone marrow. Further provided herein is a pharmaceutical composition comprising a population of cells of the embodiments. Also provided herein is a composition comprising a population of cells of the embodiments for use in the treatment of a fungal infection. In some aspects, the cells are used to deliver drugs, metabolites and biomolecules at an infection site.

A further embodiment, there is provided a method of treating a fungal infection in a subject comprising administering an effective amount of cells of the embodiments to the subject. In some aspects, the fungal infection is an invasive fungal infection. In certain aspects, the invasive fungal infection is drug resistant. In some aspects, the fungal infection is caused by *Cryptococcus* sp, *C. neoformans, C. gattii,* or *Trichosporon* sp. In certain aspects, the fungal infection is caused by fungi with GXM in the cell wall. The cells may be autologous or allogeneic.

In some aspects, the subject is immunocompromised or immunocompetent. In certain aspects, the immunocompromised subject has been diagnosed with HIV/AIDS or cancer. In some aspects, the immunocompromised subject is undergoing chemotherapy or immunosuppressive therapy. In some aspects, the immunocompromised subject is a transplant recipient. In other aspects, the subject may have acquired the infection by an accident, in a war, or by natural calamities.

In additional aspects, the method further comprises administering at least a second anti-fungal agent. In some aspects, the at least a second anti-fungal agent is second anti-fungal agent is amphotericin B, caspofungin, isavuconazole, flucytosine, posaconazole, a metabolite, or a fungal cell wall degrading enzyme. In certain aspects, the cells and/or the at least a second anti-fungal agent are administered intravenously, intraperitoneally, intratracheally, intratumorally, intramuscularly, endoscopically, intralesionally, percutaneously, subcutaneously, regionally, or by direct injection or perfusion.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIGS. 12A-12E: The automated inForm® Cell Analysis™ software shows reduced area of GXM positive Titan cells in in the lungs of *C. neoformans* infected mice treated with GXMR-CAR+ T cells. The lungs of NSG mice (5 per group) were infected with *C. neoformans* yeast ($1\times10^5$/mouse) via intranasal infusion. Mice were infused intravenously with 5 million GXMR-CAR+ T cells, NoDNA T cells or PBS alone on days 1 and 4 after infection. Eight days after infection, the mice were humanely euthanized. (A) Paraffin-embedded lung tissue sections from the mice were incubated with an anti-GXM antibody and anti-mouse-FITC secondary to detect Titan cells. Images were acquired at 400× magnification using a Vectra Polaris microscope. Spectrally unmixed images showing DAPI labeled nuclei and GXM-FITC labeled Titan cells are shown. Almost no GXM-FITC cells are observed with the GXMR-CAR T cells. (B) The automated inForm® Cell Analysis™ software was utilized to quantify the area of GXM positive staining and the total area of lung tissue. Images show GXM positive Titan cells, lung tissue, and non-tissue. (C) Paraffin-embedded lung tissue sections from the mice were stained with Gomori methenamine-silver (GMS) to analyze Titan cells (black circles). The images were acquired at 200× magnification using an Olympus CKX41 microscope. (D) Graph displaying results of GXM immunofluorescence assay analyzed by the automated inForm® Cell Analysis software. The percentages of the "area of GXM positive staining/total area of lung tissue" for each mouse per group were compared using ANOVA. Pair-wised comparisons were conducted using Tukey's HSD (honestly significant difference) test. Statistical significance was defined as P value <0.05. (E) Blood cytokine levels were measured 8 days after infusion using a Bio-Rad multiplex cytokine assay. Cytokines IFN-γ and TNF-α were slightly increased in GXMR-CAR T-cells treated group when compared to NoDNA group.

DESCRIPTION OF ILLUSTRATIVE EMBODIMENTS

In certain embodiments, the present disclosure provides anti-fungal CARs and immune cells which express said CAR. The anti-fungal CAR cells provided herein may be used as a therapy to treat fungal infections, such as infections in immunocompromised patients. The immunocompromised patients may have HIV/AIDS, primary immune disorder disease (PIDD), or be transplant recipients. The fungal infection may be a drug-resistant fungal infection.

Figure 1:
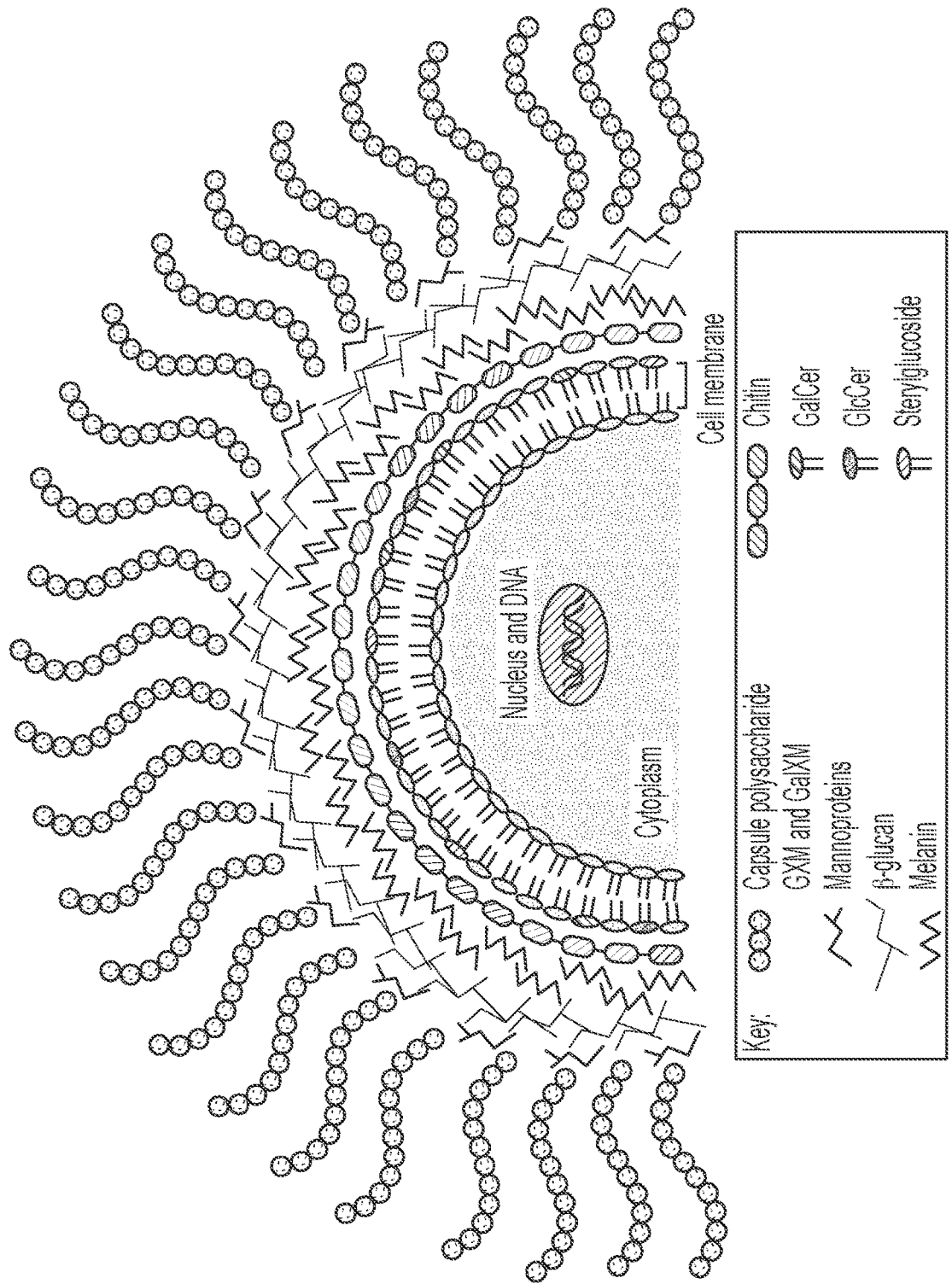
FIG. 1: A schematic diagram depicts the general capsule and cell wall structure of *Cryptococcus* sp. A single layer of plasma membrane is also present in fungi, surrounded by a cell wall that is the cover of polysaccharide capsule, which contains various layers of glucuronoxylomannan (GXM) and galactoxylomannan (GalXM).
Figure 2:
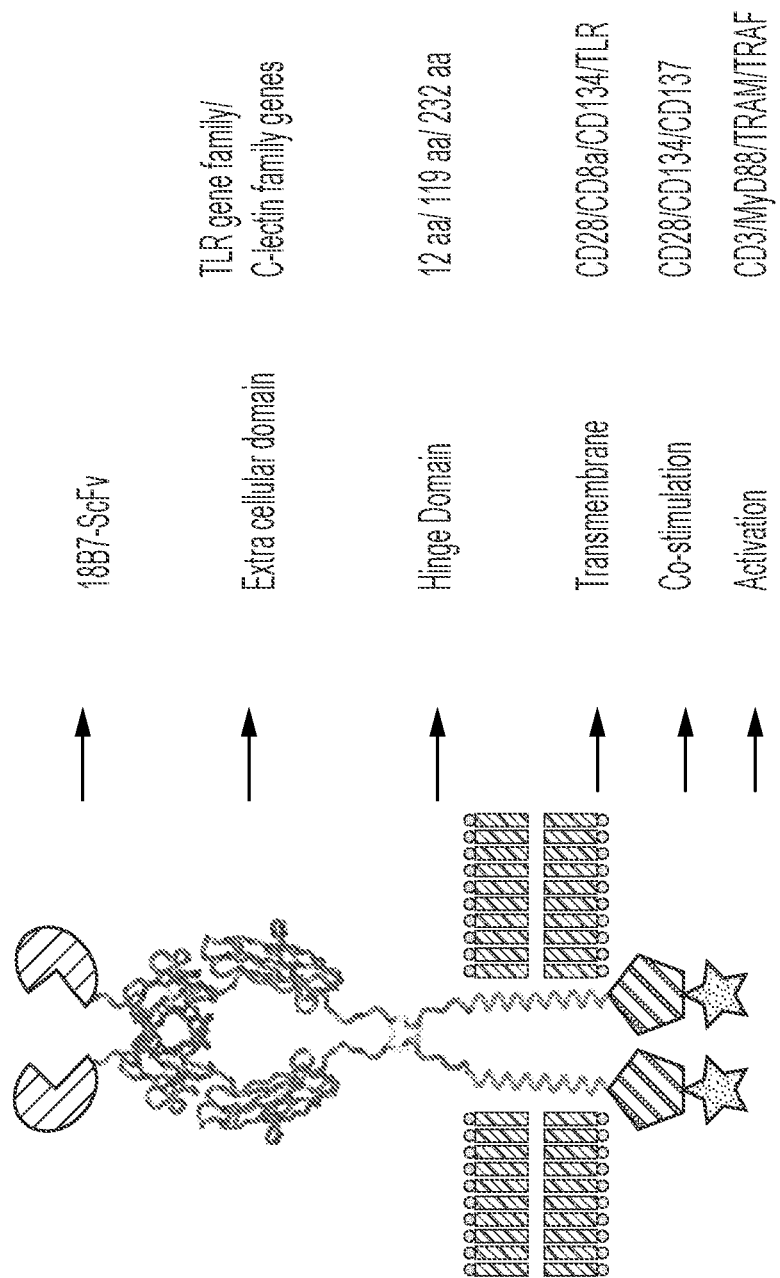
FIG. 2: A schematic representation of CARs for anti-cryptococcal therapy, designated GXMR-CAR, and the different permutations of genes used for the development of CARs.

Specifically, the present disclosure provides GXMR-CAR+ immune cells, such as T cells, and NK cells which target glucuronoxylomannan of the *Cryptococcus* sp. capsule (FIG. 1). The Crypto-CAR can comprise the extracellular domain of pathogen recognition receptors from the scFv region of an anti-GXM antibody, 18B7 clone, present on the innate cell membrane with other signaling domains, such as described in Table 1.

I. Definitions

As used herein, "essentially free," in terms of a specified component, is used herein to mean that none of the specified component has been purposefully formulated into a composition and/or is present only as a contaminant or in trace amounts. The total amount of the specified component resulting from any unintended contamination of a composition is therefore well below 0.05%, preferably below 0.01%. Most preferred is a composition in which no amount of the specified component can be detected with standard analytical methods.

As used herein the specification, "a" or "an" may mean one or more. As used herein in the claim(s), when used in conjunction with the word "comprising," the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more. The terms "about", "substantially" and "approximately" mean, in general, the stated value plus or minus 5%.

By "expression construct" or "expression cassette" is meant a nucleic acid molecule that is capable of directing transcription. An expression construct includes, at a minimum, one or more transcriptional control elements (such as promoters, enhancers or a structure functionally equivalent thereof) that direct gene expression in one or more desired cell types, tissues or organs. Additional elements, such as a transcription termination signal, may also be included.

A "vector" or "construct" (sometimes referred to as a gene delivery system or gene transfer "vehicle") refers to a macromolecule or complex of molecules comprising a polynucleotide to be delivered to a host cell, either in vitro or in vivo.

A "plasmid," a common type of a vector, is an extrachromosomal DNA molecule separate from the chromosomal DNA that is capable of replicating independently of the chromosomal DNA. In certain cases, it is circular and double-stranded.

As used herein, the term "patient" or "subject" refers to a living mammalian organism, such as a human, monkey, cow, sheep, goat, dog, cat, mouse, rat, guinea pig, or transgenic species thereof. In certain embodiments, the patient or subject is a primate. Non-limiting examples of human patients are adults, juveniles, infants and fetuses.

An "epitope" is the site on an antigen recognized by an antibody as determined by the specificity of the amino acid sequence. Two antibodies are said to bind to the same epitope if each competitively inhibits (blocks) binding of the other to the antigen as measured in a competitive binding assay. Alternatively, two antibodies have the same epitope if most amino acid mutations in the antigen that reduce or eliminate binding of one antibody reduce or eliminate binding of the other. Two antibodies are said to have overlapping epitopes if each partially inhibits binding of the other to the antigen, and/or if some amino acid mutations that reduce or eliminate binding of one antibody reduce or eliminate binding of the other.

"Treating" or treatment of a disease or condition refers to executing a protocol, which may include administering one or more drugs to a patient, in an effort to alleviate signs or symptoms of the disease. Desirable effects of treatment include decreasing the rate of disease progression, ameliorating or palliating the disease state, and remission or improved prognosis. Alleviation can occur prior to signs or symptoms of the disease or condition appearing, as well as after their appearance. Thus, "treating" or "treatment" may include "preventing" or "prevention" of disease or undesirable condition. In addition, "treating" or "treatment" does not require complete alleviation of signs or symptoms, does not require a cure, and specifically includes protocols that have only a marginal effect on the patient.

The term "effective," as that term is used in the specification and/or claims, means adequate to accomplish a desired, expected, or intended result. "Effective amount," "Therapeutically effective amount" or "pharmaceutically effective amount" when used in the context of treating a patient or subject with a compound means that amount of the compound which, when administered to a subject or patient for treating or preventing a disease, is an amount sufficient to effect such treatment or prevention of the disease.

"Treatment" or "treating" includes (1) inhibiting a disease in a subject or patient experiencing or displaying the pathology or symptomatology of the disease (e.g., arresting further development of the pathology and/or symptomatology), (2) ameliorating a disease in a subject or patient that is experiencing or displaying the pathology or symptomatology of the disease (e.g., reversing the pathology and/or symptomatology), and/or (3) effecting any measurable decrease in a disease or symptom thereof in a subject or patient that is experiencing or displaying the pathology or symptomatology of the disease.

"Prevention" or "preventing" includes: (1) inhibiting the onset of a disease in a subject or patient which may be at risk and/or predisposed to the disease but does not yet experience or display any or all of the pathology or symptomatology of the disease, and/or (2) slowing the onset of the pathology or symptomatology of a disease in a subject or patient which may be at risk and/or predisposed to the disease but does not yet experience or display any or all of the pathology or symptomatology of the disease.

As used herein, the term "framework region(s)" refers to regions of the variable region of an antibody which act as a scaffold for the CDRs. Thus, the framework regions may comprise the non-CDR sequences of the variable light chain and variable heavy chain. The CDRs of a variable region may be determined by methods known in the art, such as by using the Kabat numbering system as described in Sela-Culang et al., 2013; incorporated herein by reference in its entirety. The system described by Kabat (CITE) not only provides an unambiguous residue numbering system applicable to any variable region of an antibody, but also provides precise residue boundaries defining the three CDRs.

As generally used herein "pharmaceutically acceptable" refers to those compounds, materials, compositions, and/or dosage forms which are, within the scope of sound medical judgment, suitable for use in contact with the tissues, organs, and/or bodily fluids of human beings and animals without excessive toxicity, irritation, allergic response, or other problems or complications commensurate with a reasonable benefit/risk ratio.

"Pharmaceutically acceptable salts" means salts of compounds disclosed herein which are pharmaceutically acceptable, as defined above, and which possess the desired pharmacological activity. Such salts include acid addition salts formed with inorganic acids such as hydrochloric acid, hydrobromic acid, sulfuric acid, nitric acid, phosphoric acid, and the like; or with organic acids such as 1,2-ethanedisulfonic acid, 2-hydroxyethanesulfonic acid, 2-naphthalenesulfonic acid, 3-phenylpropionic acid, 4,4'-methylenebis(3-hydroxy-2-ene-1-carboxylic acid), 4-methylbicyclo[2.2.2]oct-2-ene-1-carboxylic acid, acetic acid, aliphatic mono- and dicarboxylic acids, aliphatic sulfuric acids, aromatic sulfuric acids, benzenesulfonic acid, benzoic acid, camphorsulfonic acid, carbonic acid, cinnamic acid, citric acid, cyclopentanepropionic acid, ethanesulfonic acid, fumaric acid, glucoheptonic acid, gluconic acid, glutamic acid, glycolic acid, heptanoic acid, hexanoic acid, hydroxynaphthoic acid, lactic acid, laurylsulfuric acid, maleic acid, malic acid, malonic acid, mandelic acid, methanesulfonic acid, muconic acid, o-(4-hydroxybenzoyl)benzoic acid, oxalic acid, p-chlorobenzenesulfonic acid, phenyl-substituted alkanoic acids, propionic acid, p-toluenesulfonic acid, pyruvic acid, salicylic acid, stearic acid, succinic acid, tartaric acid, tertiarybutylacetic acid, trimethylacetic acid, and the like. Pharmaceutically acceptable salts also include base addition salts which may be formed when acidic protons present are capable of reacting with inorganic or organic bases. Acceptable inorganic bases include sodium hydroxide, sodium carbonate, potassium hydroxide, aluminum hydroxide and calcium hydroxide. Acceptable organic bases include ethanolamine, diethanolamine, triethanolamine, tromethamine, N methylglucamine and the like. It should be recognized that the particular anion or cation forming a part of any salt of this invention is not critical, so long as the salt, as a whole, is pharmacologically acceptable. Additional examples of pharmaceutically acceptable salts and their methods of preparation and use are presented in *Handbook of Pharmaceutical Salts: Properties, and Use* (P. H. Stahl & C. G. Wermuth eds., Verlag Helvetica Chimica Acta, 2002).

A "pharmaceutically acceptable carrier," "drug carrier," or simply "carrier" is a pharmaceutically acceptable substance formulated along with the active ingredient medication that is involved in carrying, delivering and/or transporting a chemical agent. Drug carriers may be used to improve the delivery and the effectiveness of drugs, including for example, controlled-release technology to modulate drug bioavailability, decrease drug metabolism, and/or reduce drug toxicity. Some drug carriers may increase the effectiveness of drug delivery to the specific target sites. Examples of carriers include: liposomes, microspheres (e.g., made of poly(lactic-co-glycolic) acid), albumin microspheres, synthetic polymers, nanofibers, protein-DNA complexes, protein conjugates, erythrocytes, virosomes, and dendrimers.

The term "chimeric antigen receptors (CARs)," as used herein, may refer to artificial T cell receptors, chimeric T cell receptors, chimeric NK cell receptor or chimeric immunoreceptors, for example, and encompass engineered receptors that graft an artificial specificity onto a particular immune effector cell. CARs may be employed to impart the specificity of a monoclonal antibody onto a T cell, thereby allowing a large number of specific T cells to be generated, for example, for use in adoptive cell therapy. In specific embodiments, CARs direct specificity of the cell to a tumor associated antigen, for example. In some embodiments, CARs comprise an intracellular activation domain, a transmembrane domain, and an extracellular domain comprising a tumor associated antigen binding region. In particular aspects, CARs comprise fusions of single-chain variable fragments (scFv) derived from monoclonal antibodies, fused to CD3-zeta a transmembrane domain and endodomain. The specificity of other CAR designs may be derived from ligands of receptors (e.g., peptides) or from pattern-recognition receptors, such as Dectins. In certain cases, the spacing of the antigen-recognition domain can be modified to reduce activation-induced cell death. In certain cases, CARs comprise domains for additional co-stimulatory signaling, such as CD3ζ, FcR, CD27, CD28, CD137, DAP10, and/or OX40. In some cases, molecules can be co-expressed with the CAR, including co-stimulatory molecules, reporter genes for imaging (e.g., for positron emission tomography), gene products that conditionally ablate the T cells upon addition of a pro-drug, homing receptors, chemokines, chemokine receptors, cytokines, and cytokine receptors.

The term "antigen presenting cells (APCs)" refers to a class of cells capable of presenting one or more antigens in the form of peptide-MHC complex recognizable by specific effector cells of the immune system, and thereby inducing an effective cellular immune response against the antigen or antigens being presented. APCs can be intact whole cells such as macrophages, B-cells, endothelial cells, activated T-cells, and dendritic cells; or other molecules, naturally occurring or synthetic, such as purified MHC Class I molecules complexed to β2-microglobulin. While many types of cells may be capable of presenting antigens on their cell surface for T-cell recognition, only dendritic cells have the capacity to present antigens in an efficient amount to activate naive T-cells for cytotoxic T-lymphocyte (CTL) responses.

The term "culturing" refers to the in vitro maintenance, differentiation, and/or propagation of cells in suitable media. By "enriched" is meant a composition comprising cells present in a greater percentage of total cells than is found in the tissues where they are present in an organism.

A polynucleotide or polynucleotide region (or a polypeptide or polypeptide region) has a certain percentage (for example, 80%, 85%, 90%, or 95%) of "sequence identity" or "homology" to another sequence means that, when aligned, that percentage of bases (or amino acids) are the same in comparing the two sequences. This alignment and the percent homology or sequence identity can be determined using software programs known in the art, for example those described in CURRENT PROTOCOLS IN MOLECULAR BIOLOGY (F. M. Ausubel et al., eds., 1987) Supplement 30, section 7.7.18, Table 7.7.1. Preferably, default parameters are used for alignment. A preferred alignment program is BLAST, using default parameters. In particular, preferred programs are BLASTN and BLASTP, using the following default parameters: Genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+SwissProtein+SPupdate+PIR.

II. Immune Cells

Certain embodiments of the present disclosure concern immune cells which express a specific receptor for GXM. The immune cells may be T cells (e.g., regulatory T cells, CD4+ T cells, CD8+ T cells, or gamma-delta T cells), B cells, NK cells, invariant NK cells, NKT cells, stem cells (e.g., mesenchymal stem cells (MSCs) or induced pluripotent stem (iPSC) cells). In some embodiments, the cells are monocytes or granulocytes, e.g., myeloid cells, macrophages, neutrophils, dendritic cells, mast cells, eosinophils, and/or basophils. In particular aspects, the immune cells for CAR expression are T cells (e.g., αβ T cells, such as CD4 and CD8 cells, γδ T cells, regulatory T cells, T17 cells, Tfh cells, Th1, and Th2 cells), NK cells, macrophages, dendritic cells (e.g., derived from autologous PBMC, cord blood PBMC and donor PBMC), lymphocytes and myelocytes, such as derived from the tumor microenvironment. Other cells include T cell cancer cell lines, such as Jurkat cells, and NK cell lines, such as NK-92 and its derivatives and KHYG-1 and its derivatives, and macrophage cell lines, such as U937. Also provided herein are methods of producing and engineering the immune cells as well as methods of using and administering the cells for adoptive cell therapy, in which case the cells may be autologous or allogeneic. Thus, the immune cells may be used as immunotherapy, such as to treat fungal infections.

The immune cells may be isolated from subjects, particularly human subjects. The immune cells can be obtained from a subject of interest, such as a subject suspected of having a particular disease or condition, a subject suspected of having a predisposition to a particular disease or condition, or a subject who is undergoing therapy for a particular disease or condition. Immune cells can be collected from any location in which they reside in the subject including, but not limited to, blood, cord blood, spleen, thymus, lymph nodes, and bone marrow. The isolated immune cells may be used directly, or they can be stored for a period of time, such as by freezing.

The immune cells may be enriched/purified from any tissue where they reside including, but not limited to, blood (including blood collected by blood banks or cord blood banks), spleen, bone marrow, tissues removed and/or exposed during surgical procedures, and tissues obtained via biopsy procedures. Tissues/organs from which the immune cells are enriched, isolated, and/or purified may be isolated from both living and non-living subjects, wherein the non-living subjects are organ donors.

The population of immune cells can be obtained from a subject in need of therapy or suffering from a disease associated with reduced immune cell activity. Thus, the cells will be autologous to the subject in need of therapy. Alternatively, the population of immune cells can be obtained from a donor, preferably a histocompatibility matched donor. The immune cell population can be harvested from the peripheral blood, cord blood, bone marrow, spleen, or any other organ/tissue in which immune cells reside in said subject or donor.

When the population of immune cells is obtained from a donor distinct from the subject, the donor is preferably allogeneic, provided the cells obtained are subject-compatible in that they can be introduced into the subject. Allogeneic donor cells are may or may not be human-leukocyte-antigen (HLA)-compatible.

In some embodiments, the immune cells are T cells. Several basic approaches for the derivation, activation and expansion of functional anti-tumor effector cells have been described in the last two decades. These include: autologous cells, such as tumor-infiltrating lymphocytes (TILs); T cells activated ex-vivo using autologous DCs, lymphocytes, artificial antigen-presenting cells (APCs) or beads coated with T cell ligands and activating antibodies, or cells isolated by virtue of capturing target cell membrane; allogeneic cells naturally expressing anti-host tumor T cell receptor (TCR); and non-tumor-specific autologous or allogeneic cells genetically reprogrammed or "redirected" to express tumor-reactive TCR or chimeric TCR molecules displaying antibody-like tumor recognition capacity known as "T-bodies". These approaches have given rise to numerous protocols for T cell preparation and immunization which can be used in the methods described herein.

In some embodiments, the T cells are derived from the blood, bone marrow, lymph, umbilical cord, or lymphoid organs. In some aspects, the cells are human cells. The cells typically are primary cells, such as those isolated directly from a subject and/or isolated from a subject and frozen. In some embodiments, the cells include one or more subsets of T cells or other cell types, such as whole T cell populations, CD4$^+$ cells, CD8$^+$ cells, and subpopulations thereof, such as those defined by function, activation state, maturity, potential for differentiation, expansion, recirculation, localization, and/or persistence capacities, antigen-specificity, type of antigen receptor, presence in a particular organ or compartment, marker or cytokine secretion profile, and/or degree of differentiation. With reference to the subject to be treated, the cells may be allogeneic and/or autologous. In some embodiments, the methods include isolating cells from the subject, preparing, processing, culturing, and/or engineering them, as described herein, and re-introducing them into the same patient, before or after cryopreservation.

Among the sub-types and subpopulations of T cells (e.g., CD4$^+$ and/or CD8$^+$ T cells) are naive T ($T_N$) cells, effector T cells ($T_{EFF}$), memory T cells and sub-types thereof, such as stem cell memory T ($TSC_M$), central memory T ($TC_M$), effector memory T ($T_{EM}$), or terminally differentiated effector memory T cells, tumor-infiltrating lymphocytes (TIL), immature T cells, mature T cells, helper T cells, cytotoxic T cells, mucosa-associated invariant T (MAIT) cells, naturally occurring and adaptive regulatory T (Treg) cells, helper T cells, such as TH1 cells, TH2 cells, TH3 cells, TH17 cells, TH9 cells, TH22 cells, follicular helper T cells, alpha/beta T cells, and delta/gamma T cells.

In some embodiments, one or more of the T cell populations is enriched for or depleted of cells that are positive for a specific marker, such as surface markers, or that are negative for a specific marker. In some cases, such markers are those that are absent or expressed at relatively low levels on certain populations of T cells (e.g., non-memory cells) but are present or expressed at relatively higher levels on certain other populations of T cells (e.g., memory cells).

In some embodiments, T cells are separated from a PBMC sample by negative selection of markers expressed on non-T cells, such as B cells, monocytes, or other white blood cells, such as CD14. In some aspects, a CD4$^+$ or CD8$^+$ selection step is used to separate CD4$^+$ helper and CD8$^+$ cytotoxic T cells. Such CD4$^+$ and CD8$^+$ populations can be further sorted into sub-populations by positive or negative selection for markers expressed or expressed to a relatively higher degree on one or more naive, memory, and/or effector T cell subpopulations.

In some embodiments, CD8$^+$ T cells are further enriched for or depleted of naive, central memory, effector memory, and/or central memory stem cells, such as by positive or negative selection based on surface antigens associated with the respective subpopulation. In some embodiments, enrichment for central memory T ($T_{CM}$) cells is carried out to increase efficacy, such as to improve long-term survival, expansion, and/or engraftment following administration, which in some aspects is particularly robust in such subpopulations.

In some embodiments, the T cells are autologous T cells. In this method, tumor samples are obtained from patients and a single cell suspension is obtained. The single cell suspension can be obtained in any suitable manner, e.g., mechanically (disaggregating the tumor using, e.g., a gentleMACS™ Dissociator, Miltenyi Biotec, Auburn, Calif.) or enzymatically (e.g., collagenase or DNase). Single-cell suspensions of tumor enzymatic digests are cultured in interleukin-2 (IL-2).

The cultured T cells can be pooled and rapidly expanded. Rapid expansion provides an increase in the number of antigen-specific T-cells of at least about 50-fold (e.g., 50-, 60-, 70-, 80-, 90-, or 100-fold, or greater) over a period of about 10 to about 14 days. More preferably, rapid expansion provides an increase of at least about 200-fold (e.g., 200-, 300-, 400-, 500-, 600-, 700-, 800-, 900-, or greater) over a period of about 10 to about 14 days.

Expansion can be accomplished by any of a number of methods as are known in the art. For example, T cells can be rapidly expanded using non-specific T-cell receptor stimulation in the presence of feeder lymphocytes and either interleukin-2 (IL-2) or interleukin-15 (IL-15), with IL-2 being preferred. The non-specific T cell receptor stimulus can include around 30 ng/ml of OKT3, a mouse monoclonal anti-CD3 antibody (available from Ortho-McNeil®, Raritan, N.J.). Alternatively, T cells can be rapidly expanded by stimulation of peripheral blood mononuclear cells (PBMC) in vitro with one or more antigens (including antigenic portions thereof, such as epitope(s), or a cell) of the cancer, which can be optionally expressed from a vector, such as an human leukocyte antigen A2 (HLA-A2) binding peptide, in the presence of a T cell growth factor.

The autologous T cells can be modified to express a T cell growth factor that promotes the growth and activation of the autologous T cells. Suitable T cell growth factors include, for example, interleukin (IL)-2, IL-7, IL-15, and IL-12. Suitable methods of modification are known in the art. See, for instance, Sambrook et al., *Molecular Cloning: A Laboratory Manual*, 3$^{rd}$ ed., Cold Spring Harbor Press, Cold Spring Harbor, N.Y. 2001; and Ausubel et al., *Current Protocols in Molecular Biology*, Greene Publishing Associates and John Wiley & Sons, NY, 1994. In particular aspects, modified autologous T cells express the T cell growth factor at high levels.

III. Chimeric Antigen Receptors

The present disclosure provides GXMR-CARs which comprise a binding domain to GXM, such as scFv from anti-GXM antibody 18B7 clone. The anti-scFv may have 80%, 85%, 86%, 87%, 88%, 89%, 90%, 91%, 92%, 93%, 94%, 95%, 96%, 97%, 98%, or 100% sequence identity to the scFv of SEQ ID Nos: 1-2 (i.e., the scFv of the 18B7 antibody). The GXMR-CAR may have 80%, 85%, 86%, 87%, 88%, 89%, 90%, 91%, 92%, 93%, 94%, 95%, 96%, 97%, 98%, or 100% sequence identity to the CAR of SEQ ID NO:3. In some embodiments, the CAR contains an extracellular antigen-recognition domain that specifically binds to GXM.

In some embodiments, the chimeric antigen receptor comprises: a) an intracellular signaling domain, b) a hinge (linker) and transmembrane domain and c) an extracellular domain comprising an antigen binding region.

In some embodiments, the engineered antigen receptors include chimeric antigen receptors (CARs), including activating or stimulatory CARs, costimulatory CARs (see WO2014/055668), and/or inhibitory CARs (iCARs). The CARs generally include an extracellular antigen (or ligand) binding domain linked to one or more intracellular signaling components, in some aspects via linkers and/or transmembrane domain(s). Such molecules typically mimic or approximate a signal through a natural antigen receptor, a signal through such a receptor in combination with a costimulatory receptor, and/or a signal through a costimulatory receptor alone.

Certain embodiments of the present disclosure concern the use of nucleic acids, including nucleic acids encoding an antigen-specific CAR polypeptide, including a CAR that has been humanized to reduce immunogenicity (hCAR), comprising an intracellular signaling domain, a transmembrane domain, and an extracellular domain comprising one or more signaling motifs. In certain embodiments, the CAR may recognize an epitope comprising the shared space between one or more antigens. In certain embodiments, the binding region can comprise complementary determining regions of a monoclonal antibody, variable regions of a monoclonal antibody, and/or antigen binding fragments thereof. In another embodiment, that specificity is derived from a peptide (e.g., cytokine) that binds to a receptor.

It is contemplated that the human CAR nucleic acids may be human genes used to enhance cellular immunotherapy for human patients. In a specific embodiment, the invention includes a full-length CAR cDNA or coding region. The antigen binding regions or domain can comprise a fragment of the $V_H$ and $V_L$ chains of a single-chain variable fragment (scFv) derived from a particular human monoclonal antibody. The fragment can also be any number of different antigen binding domains of a human antigen-specific antibody. In a more specific embodiment, the fragment is an antigen-specific scFv encoded by a sequence that is optimized for human codon usage for expression in human cells.

The arrangement could be multimeric, such as a diabody or multimers. The multimers are most likely formed by cross pairing of the variable portion of the light and heavy chains into a diabody. The hinge portion of the construct can have multiple alternatives from being totally deleted, to having the first cysteine maintained, to a proline rather than a serine substitution, to being truncated up to the first cysteine. The Fc portion can be deleted. Any protein that is stable and/or dimerizes can serve this purpose. One could use just one of the Fc domains, e.g., either the CH2 or CH3 domain from human immunoglobulin. One could also use the hinge, CH2 and CH3 region of a human immunoglobulin that has been modified to improve dimerization. One could also use just the hinge portion of an immunoglobulin. One could also use portions of CD8alpha.

In some embodiments, the CAR nucleic acid comprises a sequence encoding other costimulatory receptors, such as a transmembrane domain and a modified CD28 intracellular signaling domain. Other costimulatory receptors include, but are not limited to one or more of CD28, CD27, OX-40 (CD134), DAP10, DAP12, NKG2D, CARD9 and 4-1BB (CD137). In addition to a primary signal initiated by CD33, an additional signal provided by a human costimulatory receptor inserted in a human CAR is important for full activation of NK cells and could help improve in vivo persistence and the therapeutic success of the adoptive immunotherapy.

The sequence of the open reading frame encoding the chimeric receptor can be obtained from a genomic DNA source, a cDNA source, or can be synthesized (e.g., via PCR), or combinations thereof. Depending upon the size of the genomic DNA and the number of introns, it may be desirable to use cDNA or a combination thereof as it is found that introns stabilize the mRNA. Also, it may be further advantageous to use endogenous or exogenous non-coding regions to stabilize the mRNA.

It is contemplated that the chimeric construct can be introduced into immune cells as naked DNA or in a suitable vector. Methods of stably transfecting cells by electroporation using naked DNA are known in the art. Naked DNA generally refers to the DNA encoding a chimeric receptor contained in a plasmid expression vector in proper orientation for expression.

Alternatively, a viral vector (e.g., a retroviral vector, adenoviral vector, adeno-associated viral vector, or lentiviral vector) can be used to introduce the chimeric construct into immune cells. Suitable vectors for use in accordance with the method of the present disclosure are non-replicating in the immune cells. A large number of vectors are known that are based on viruses, where the copy number of the virus maintained in the cell is low enough to maintain the viability of the cell, such as, for example, vectors based on HIV, SV40, EBV, HSV, or BPV.

In some aspects, the antigen-specific binding, or recognition component is linked to one or more transmembrane and intracellular signaling domains. In some embodiments, the CAR includes a transmembrane domain fused to the extracellular domain of the CAR. In one embodiment, the transmembrane domain that naturally is associated with one of the domains in the CAR is used. In some instances, the transmembrane domain is selected or modified by amino acid substitution to avoid binding of such domains to the transmembrane domains of the same or different surface membrane proteins to minimize interactions with other members of the receptor complex.

The transmembrane domain in some embodiments is derived either from a natural or from a synthetic source. Where the source is natural, the domain in some aspects is derived from any membrane-bound or transmembrane protein. Transmembrane regions include those derived from (i.e. comprise at least the transmembrane region(s) of) the alpha, beta or zeta chain of the T-cell receptor, CD28, CD3 zeta, CD3 epsilon, CD3 gamma, CD3 delta, CD45, CD4, CD5, CD8, CD9, CD 16, CD22, CD33, CD37, CD64, CD80, CD86, CD 134, CD137, CD154, ICOS/CD278, GITR/CD357, NKG2D, and DAP molecules. Alternatively, the transmembrane domain in some embodiments is synthetic. In some aspects, the synthetic transmembrane domain comprises predominantly hydrophobic residues such as leucine and valine. In some aspects, a triplet of phenylalanine, tryptophan and valine will be found at each end of a synthetic transmembrane domain.

IV. Methods of Use

Fungal infections pose a significant threat to the human population by affecting over a billion people worldwide. Despite the availability of anti-fungal drugs, invasive fungal infections are associated with high mortality rates worldwide, causing an estimated 1.5 million deaths each year, a number comparable to tuberculosis. Thus, the present disclosure further provides methods of treating fungal infections by administering an effective amount of GXMR-CAR-cell, such as CAR-T cells or CAR-NK cells, to a subject. The subject may be immunocompromised patients, such as those living with HIV/AIDS, cancer patients who are receiving chemotherapy, primary immune disorder (genetic disorder) disease patients or solid organ transplant patients who are taking immunosuppressive drugs.

In certain embodiments of the present disclosure, immune cells are delivered to an individual in need thereof, such as an individual that has cancer or a fungal infection. The cells then enhance the individual's immune system to attack the respective cancer or pathogenic cells. In some cases, the individual is provided with one or more doses of the immune cells. In cases where the individual is provided with two or more doses of the immune cells, the duration between the administrations should be sufficient to allow time for propagation in the individual, and in specific embodiments the duration between doses is 1, 2, 3, 4, 5, 6, 7, or more days.

In yet another embodiment, the subject is the recipient of a transplanted organ or stem cells and immune cells are used to prevent and/or treat rejection. In particular embodiments, the subject has or is at risk of developing graft versus host disease. Any of the populations of immune cells disclosed herein can be utilized. Examples of a transplanted organ include a solid organ transplant, such as kidney, liver, skin, pancreas, lung and/or heart, or a cellular transplant such as islets, hepatocytes, myoblasts, bone marrow, or hematopoietic or other stem cells. The transplant can be a composite transplant, such as tissues of the face. Immune cells can be administered prior to transplantation, concurrently with transplantation, or following transplantation. In some embodiments, the immune cells are administered prior to the transplant, such as at least 1 hour, at least 12 hours, at least 1 day, at least 2 days, at least 3 days, at least 4 days, at least 5 days, at least 6 days, at least 1 week, at least 2 weeks, at least 3 weeks, at least 4 weeks, or at least 1 month prior to the transplant. In one specific, non-limiting example, administration of the therapeutically effective amount of immune cells occurs 3-5 days prior to transplantation.

In certain embodiments, a growth factor that promotes the growth and activation of the immune cells is administered to the subject either concomitantly with the immune cells or subsequently to the immune cells. The immune cell growth factor can be any suitable growth factor that promotes the growth and activation of the immune cells. Examples of suitable immune cell growth factors include interleukin (IL)-2, IL-7, IL-15, and IL-12, which can be used alone or in various combinations, such as IL-2 and IL-7, IL-2 and IL-15, IL-7 and IL-15, IL-2, IL-7 and IL-15, IL-12 and IL-7, IL-12 and IL-15, or IL-12 and IL2.

Therapeutically effective amounts of immune cells can be administered by a number of routes, including parenteral administration, for example, intravenous, intraperitoneal, intramuscular, intrasternal, or intraarticular injection, or infusion.

The therapeutically effective amount of immune cells for use in adoptive cell therapy is that amount that achieves a desired effect in a subject being treated. For instance, this can be the amount of immune cells necessary to inhibit advancement, or to cause regression of a fungal infection, or which is capable of relieving symptoms caused by a fungal infection, such as pain and inflammation. It can be the amount necessary to relieve symptoms associated with inflammation, such as pain, edema and elevated temperature. It can also be the amount necessary to diminish or prevent rejection of a transplanted organ.

The immune cell population can be administered in treatment regimens consistent with the disease, for example a single or a few doses over one to several days to ameliorate a disease state or periodic doses over an extended time to inhibit disease progression and prevent disease recurrence. The precise dose to be employed in the formulation will also depend on the route of administration, and the seriousness of the disease or disorder, and should be decided according to the judgment of the practitioner and each patient's circumstances. The therapeutically effective amount of immune cells will be dependent on the subject being treated, the severity and type of the affliction, and the manner of administration. In some embodiments, doses that could be used in the treatment of human subjects range from at least $3.8 \times 10^4$, at least $3.8 \times 10^5$, at least $3.8 \times 10^6$, at least $3.8 \times 10^7$, at least $3.8 \times 10^8$, at least $3.8 \times 10^9$, or at least $3.8 \times 10^{10}$ immune cells/m$^2$. In a certain embodiment, the dose used in the treatment of human subjects ranges from about $3.8 \times 10^9$ to about $3.8 \times 10^{10}$ immune cells/m$^2$. In additional embodiments, a therapeutically effective amount of immune cells can vary from about $5 \times 10^6$ cells per kg body weight to about $7.5 \times 10^8$ cells per kg body weight, such as about $2 \times 10^7$ cells to about $5 \times 10^8$ cells per kg body weight, or about $5 \times 10^7$ cells to about $2 \times 10^8$ cells per kg body weight. The exact amount of immune cells is readily determined by one of skill in the art based on the age, weight, sex, and physiological condition of the subject. Effective doses can be extrapolated from dose-response curves derived from in vitro or animal model test systems.

The immune cells may be administered in combination with one or more other therapeutic agents for the treatment of the fungal infection. Combination therapies can include, but are not limited to, one or more anti-microbial agents (for example, antibiotics, anti-viral agents and anti-fungal agents), fungal cell wall degrading enzymes such as Chitinase and β-Glucanase; anti-tumor agents (for example, fluorouracil, methotrexate, paclitaxel, fludarabine, etoposide, doxorubicin, or vincristine), cytokines (for example, interleukin-10 or transforming growth factor-beta), hormones (for example, estrogen), or a vaccine. In addition, immunosuppressive or tolerogenic agents including but not limited to calcineurin inhibitors (e.g., cyclosporin and tacrolimus); mTOR inhibitors (e.g., Rapamycin); mycophenolate mofetil, antibodies (e.g., recognizing IVIG, or B cells); chemotherapeutic agents (e.g., Methotrexate, Treosulfan, Busulfan); irradiation; or chemokines, interleukins or their inhibitors (e.g., BAFF, IL-2, anti-IL-2R, IL-4, JAK kinase inhibitors) can be administered. Such additional pharmaceutical agents can be administered before, during, or after administration of the immune cells, depending on the desired effect. This administration of the cells and the agent can be by the same route or by different routes, and either at the same site or at a different site.

Also provided herein are pharmaceutical compositions and formulations comprising immune cells (e.g., T cells or NK cells) and a pharmaceutically acceptable carrier to deliver drugs, metabolites and biomolecules at the infection site on demand.

Pharmaceutical compositions and formulations as described herein can be prepared by mixing the active ingredients (such as an antibody or a polypeptide) having the desired degree of purity with one or more optional pharmaceutically acceptable carriers (Remington's Pharmaceutical Sciences 22$^{nd}$ edition, 2012), in the form of lyophilized formulations or aqueous solutions. Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG).

V. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1—Development of GXMR-CAR

The monoclonal antibody was shown by immunofluorescence and agglutination studies to bind to all four serotypes of C. neoformans, opsonize C. neoformans serotypes A and D, enhance human and mouse effector cell antifungal activity, and activate the complement pathway leading to deposition of complement component 3 (C3) on the cryptococcal capsule. Administration of the 18B7 antibody to mice led to rapid clearance of serum cryptococcal antigen and deposition in the liver and spleen. Immunohistochemical studies revealed that the 18B7 antibody bound to capsular GXM in infected mouse tissues.

TABLE 1

Design elements used to generate glycan CARs using gateway system.

| Extra cellular domain | Hinge | TM domain | Signaling domain |
|---|---|---|---|
| 18B7-scFv | 12 aa | 28 | CD28 & CD3-ζ |
| | 119 aa | CD8a | CD134 & CD3-ζ |
| | 232 aa | CD134 | CD137 & CD3-ζ |
| | | CD137 | CD28 & CD134 & CD3-ζ |
| | | TLR | CD28 & CD137 & CD3-ζ |
| | | MyD88 | CD134 & CD137 & CD3-ζ |
| | | DAP9 | CD28 & OX40, & CD3-ζ |
| | | DAP10 | OX40 & CD137 & CD3-ζ |
| | | CARD9 & 10 | MyD88 & CD3-ζ |
| | | CD3 | TRAM, TRAF6 |

Figure 3:
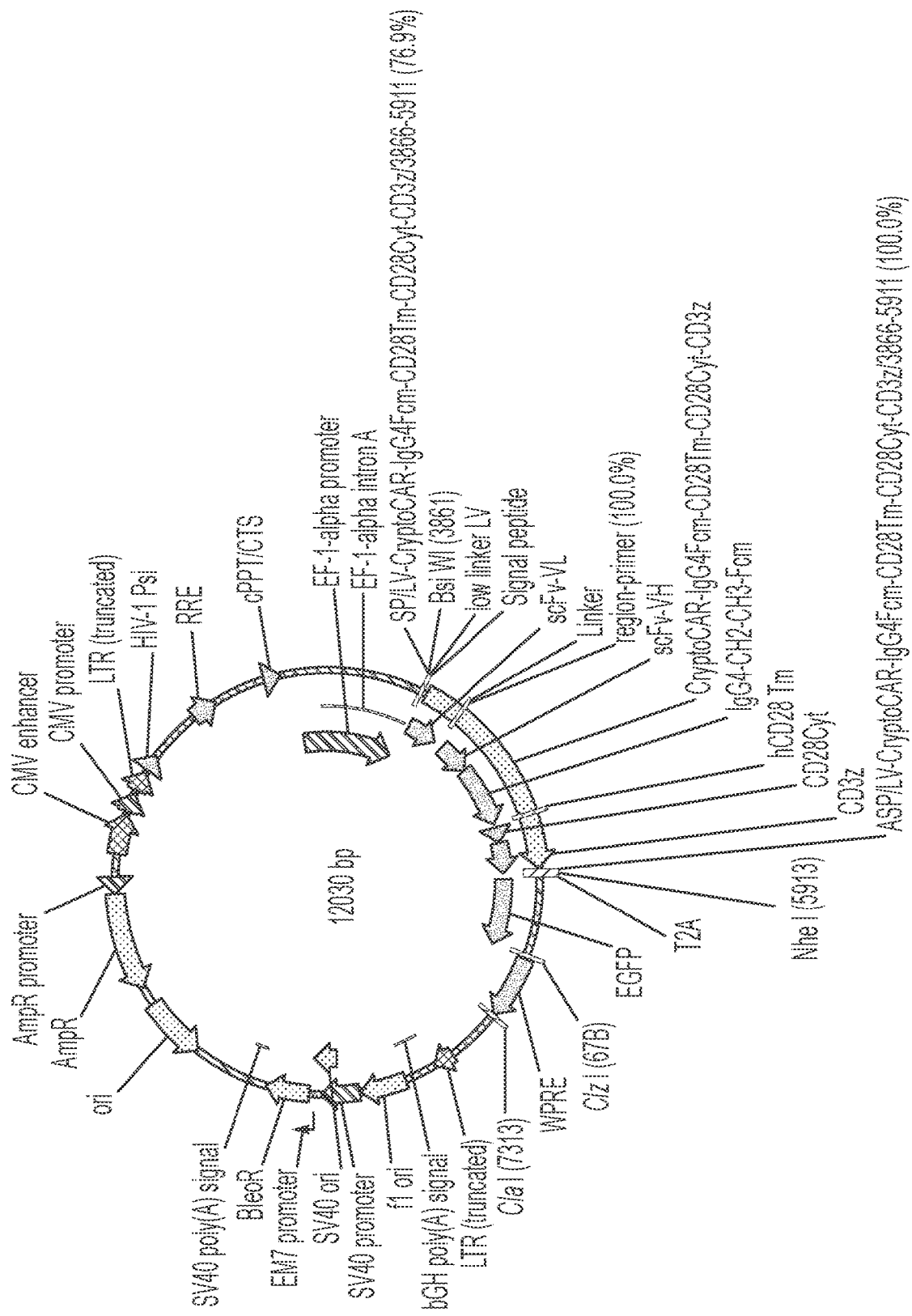
FIG. 3: Schematic representation of GXMR-CAR in lentiviral vector. It has 18B7-ScFv domain to target GXM sugar present on the *Cryptococcus* sp. capsule, IgG4-M in the spacer region, CD28TM in the transmembrane domain, CD28 as a co-stimulatory molecule and the CD3 domain for T cell activation is present in the signaling domain.

The 18B7 scFv (SEQ ID NOS: 1-2) was used to develop a GXMR-CAR. The CARs provided herein can be used to treat invasive fungal infections caused by Cryptococcus. The exemplary Crypto-CAR is shown in FIG. 3 to comprise the 18B7-ScFv domain to target the GXM sugar present on the Cryptococcus sp. capsule.

Blood samples (buffy coats) obtained at MD Anderson Blood Donor Center were used for PBMC isolation by Ficoll-Paque Plus solution (GE Healthcare Life Sciences; Cat. No. 17144002) according to the manufacturer's instructions. Transduction of PBMCs was performed using the Retronectin reagent (Takara Bio Inc.; Cat. No. T100A/B) according to the manufacturer's instructions. After transduction, the T cells were maintained in the presence of IL-2 (50 U/mL) plus IL-21 (20 ng/mL), and 10 days post-transduction the GXMR-CAR T cells expressing GFP were sorted in the core facility at MD Anderson Cancer Center. The expansion of the GXMR-CAR T cells was performed by stimulation with an antibody cocktail (anti-CD3/CD28; StemCell technologies, Cat. No. 10971) combined with IL-2 (50 U/mL) plus IL-21 (20 ng/mL).

Figures 4A, 4B:
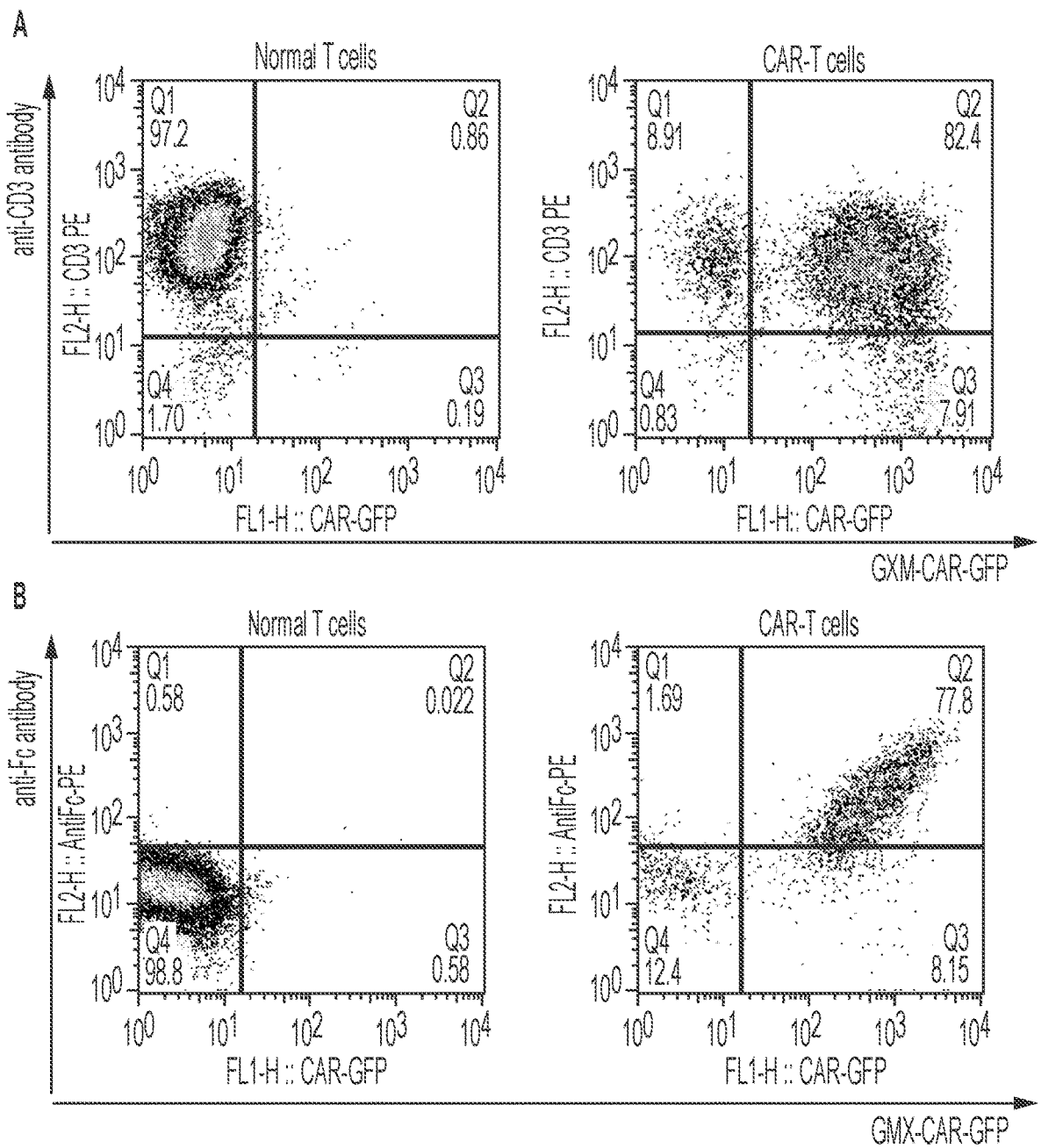
FIGS. 4A-4B: GXMR-CAR expression was detected on the surface of human T cells by flow cytometry. PBMC were stimulated with anti-CD3/CD28 antibodies and IL-2. After 3 days, the enriched T cells were transduced with GXMR-CAR lentiviral particles (CAR-T cells), and after the expansion of CAR-T cells, the percentage GXMR-CAR-GFP positive cells was determined by flow cytometry. (A) The cells were labeled with an anti-CD3 antibody (y-axis) and the double positive cells for CD3 and GFP (x-axis) were considered GFP$^+$ T cells. (B) The T cells were incubated with a PE anti-human Fc antibody (IgG4 stalk portion) and analyzed by flow cytometry; the double positive cells for anti-Fc and GFP were considered GXMR-CAR$^+$ T-cells (A and B). The negative control (Normal T cells) mock transduced cells did not receive the GXMR-CAR construct.

The GXMR-CAR construct expresses GFP (CAR-GFP) and a modified human IgG4 hinge combined with an Fc region that allows targeting with an anti-Fc antibody. The GXMR-CAR expression on the human T cell surface was analyzed by flow cytometry using a goat anti-human IgG antibody (Fc-gamma fragment specific; Jackson Immunoresearch Laboratories Inc.; Cat. No. 109-606-098) at 1:100 dilution. The percentage of the CAR T cells was determined by flow cytometry using an anti-human CD3 antibody. As shown in FIG. 4, the cells that express GXMR-CAR on the surface of human T cells can be identified as being double positive for anti-human IgG antibody and GXMR-CAR-GFP expression. The double positive GXMR-CAR cells were gated and the percentage of CD8 positive cells was analyzed. The mock transduced cells were used as negative control, designated Normal T cells.

Figure 5A:
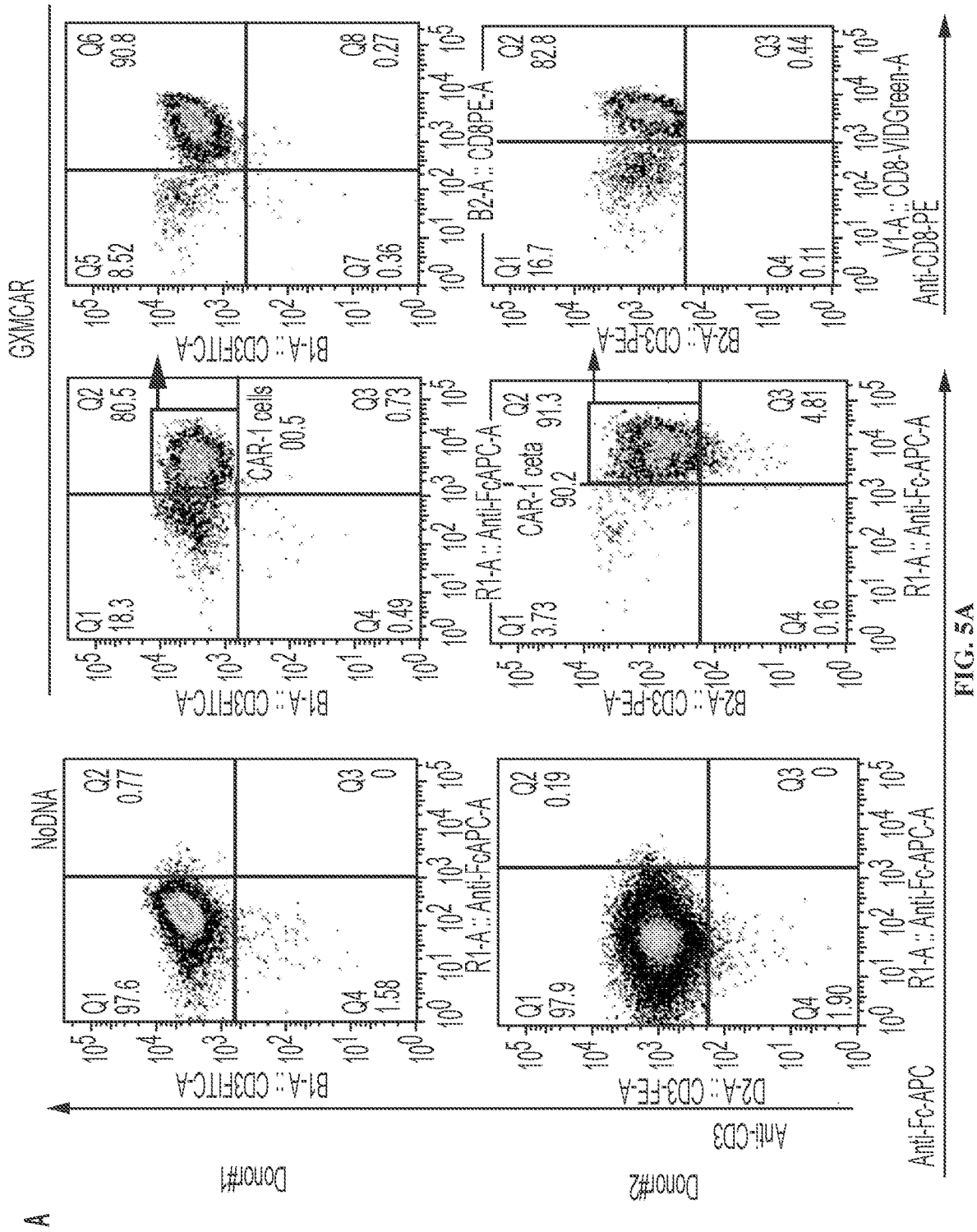
FIGS. 5A-5B: GXMR-CAR$^+$ T cell expression was assayed by flow cytometry 14 and 30 days post-electroporation. Quantification of GXMR-CAR$^+$ cells on day 14 (A) and 30 (B) of the culture was performed by flow cytometry using anti-CD3 and anti-Fc antibodies. The double positive cells for anti-CD3 and anti-Fc antibodies were considered GXMR-CAR$^+$ T cells. These cells were gated and the percentage of positive cells for anti-CD8 antibody was analyzed.
Figure 5B:
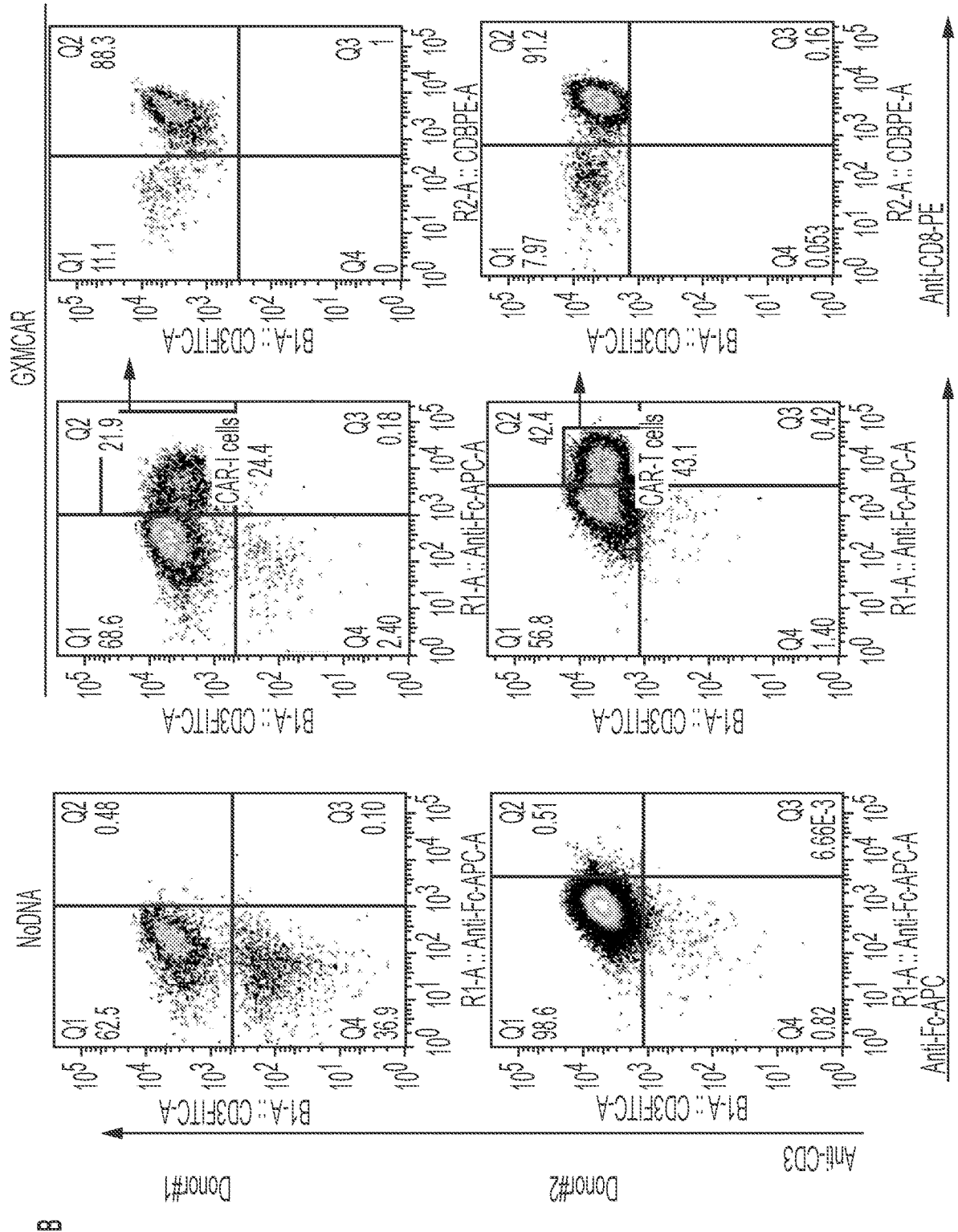
Figure 6:
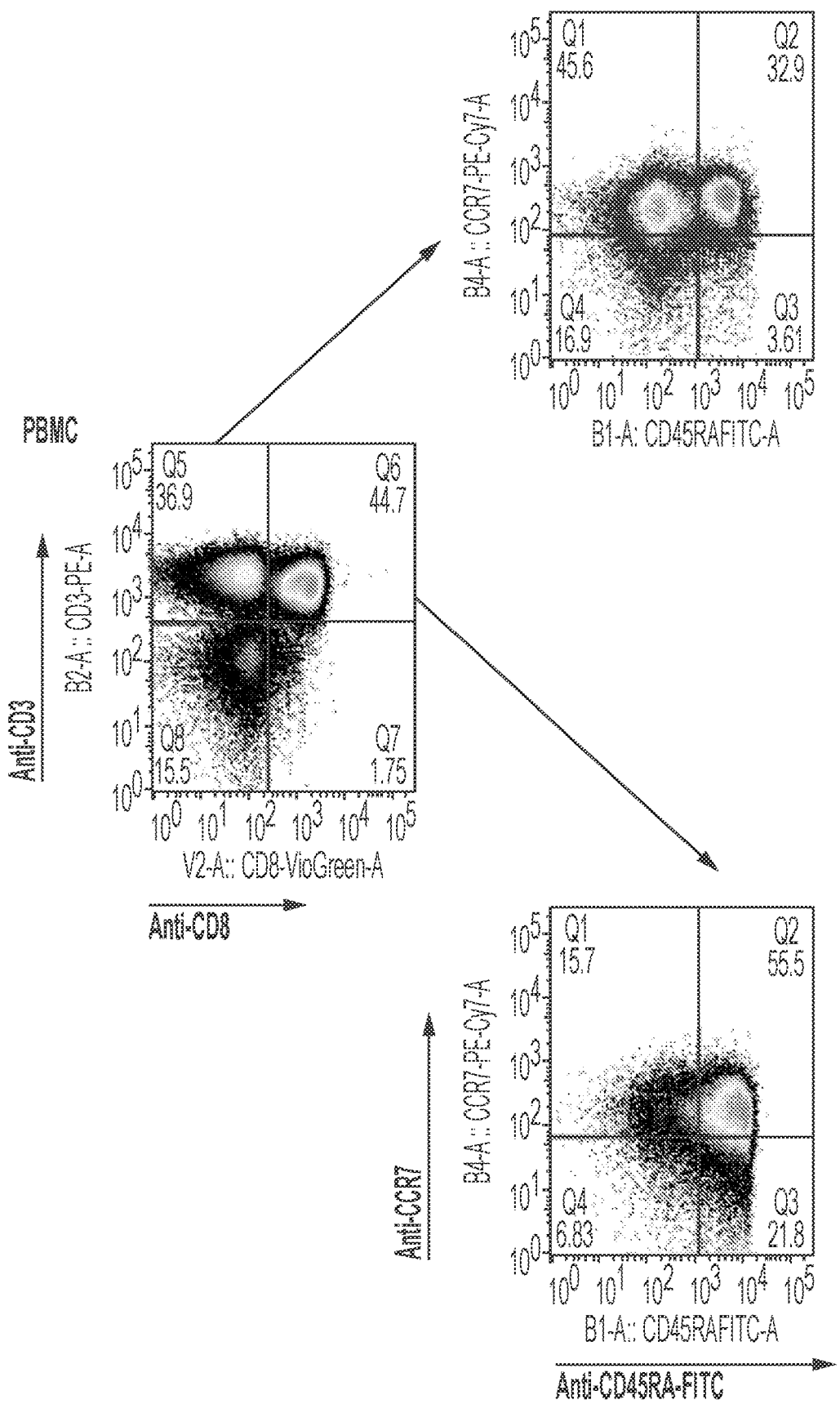
FIG. 6: Determination of phenotype of GXMR-CAR$^+$ T cells using flow cytometry. Human CD8$^+$ T cells can be divided into four populations based on their expression of CD45RA and CCR7: naive (CD45RA$^+$CCR7$^+$), central memory (CD45RA$^-$CCR7$^+$), effector memory (CD45RA$^-$CCR7$^-$), and effector (CD45RA$^+$CCR7$^-$). PBMC, NoDNA T cells, and GXMR-CAR$^+$ T cells were co-stained with anti-CD3, CD8, CD45RA, and CCR7, and analyzed by flow cytometry. CD3/CD8$^+$ gated T cells were for analyzed for expression of CD45RA and CCR7 to define the cell phenotype. Results show that PBMC and NoDNA cells were predominately naïve cells [PBMC (55.5% CD45RA$^+$CCR7$^+$), NoDNA #1 (44.7% CD45RA$^+$CCR7$^+$), and NoDNA #2 (51.9% CD45RA$^+$CCR7$^+$)]. In contrast, GXMR-CAR$^+$ T cells were mainly central memory cells [GXMR-CAR$^+$ #1, (74.8% CD45RA$^-$CCR7$^+$) and GXMR-CAR$^+$ #2 (69.0% CD45RA$^-$CCR7$^+$)].
Figure 6:
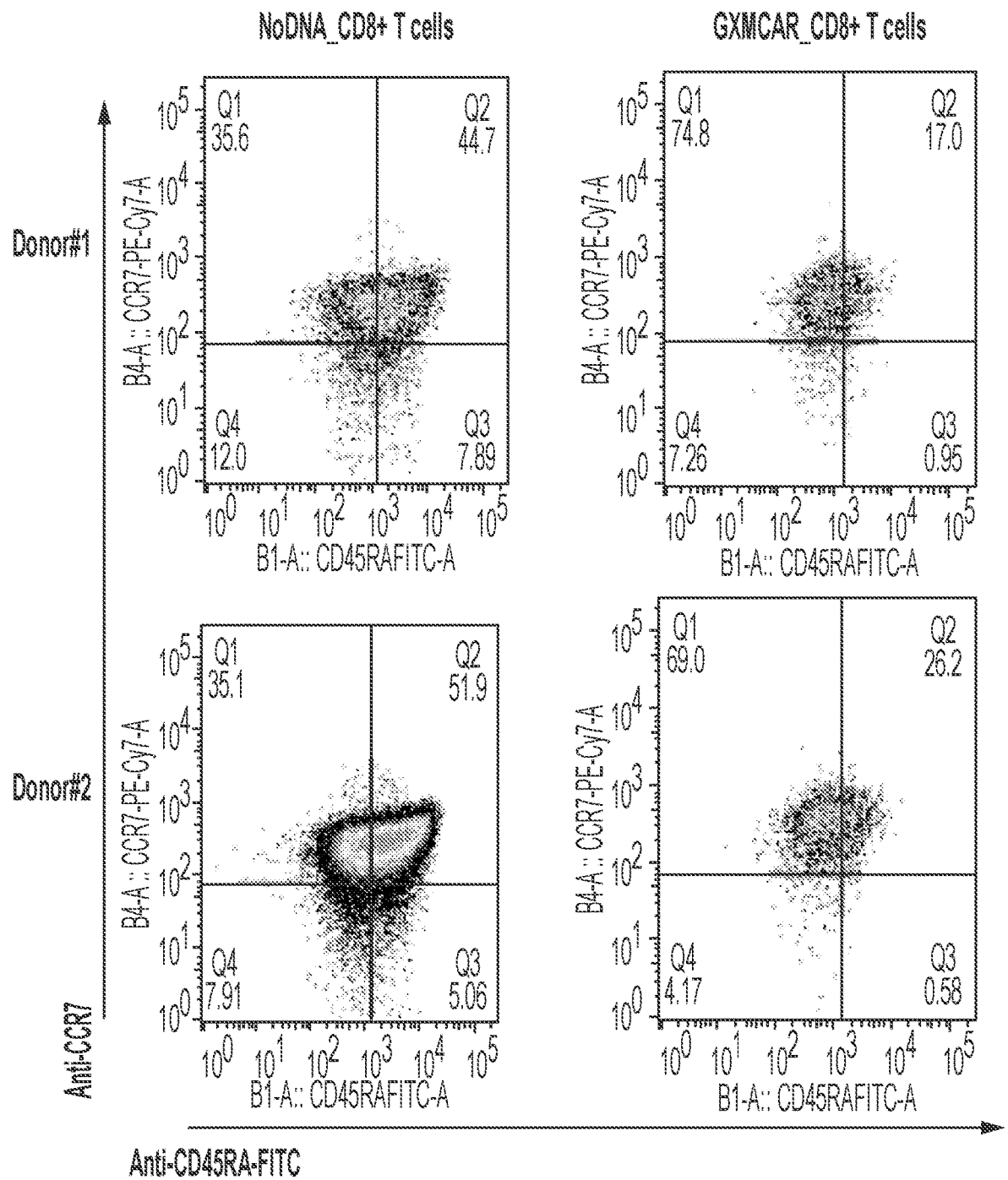

The CD8$^+$ T cells in the NoDNA T cell and GXMR-CAR T cell samples were identified by staining with anti-CD3 and anti-CD8 antibodies (FIGS. 5 and 6). Afterwards, memory T cell markers (CCR7 and CD45RA) were analyzed to determine the subpopulation of memory CD8$^+$ T cells in NoDNA T cell and GXMR-CAR T cell samples (FIG. 6).

Figure 7A:
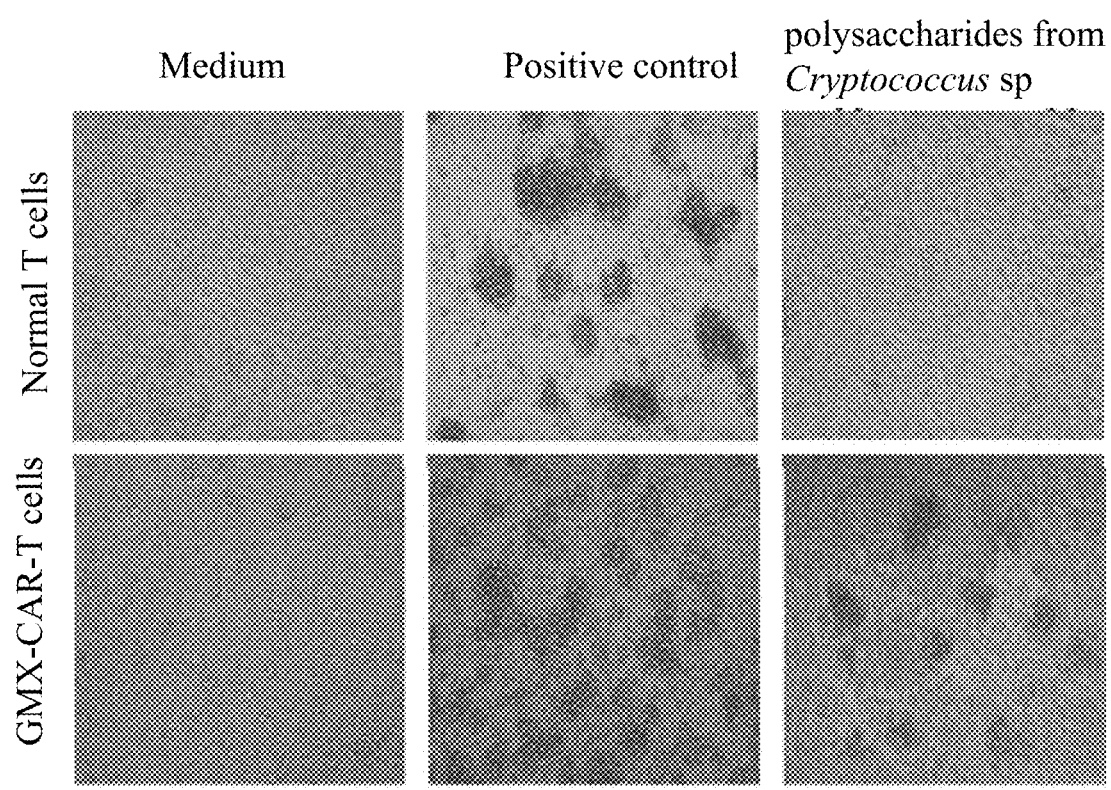
FIGS. 7A-7B: Flow cytometry assay demonstrates recognition of GXM from *Cryptococcus* sp. by GXMR-CAR$^+$ T cells. (A) Human T cells transduced with GXMR-CAR lentiviral particles and Normal cells (mock transduced cell) were incubated with a preparation of *Cryptococcus* sp. polysaccharide antigens at 1:100 dilution. After 24 h, the images were acquired by brightfield microscopy at 400× magnification. The positive control used IMMUNOCULT™ Human CD3/CD28 T cell activator to induce the human T cells activation, as manufacture's instruction (StemCell Technologies). The cells incubated with medium alone were considered as negative control. (B) The interaction of GXMR-CAR$^+$ T cells and normal T cells with *Cryptococcus* sp. polysaccharide antigens (GXM) were assayed by flow cytometry. The interaction of GXM on the CAR T cell surface was evaluated by anti-GXM monoclonal antibody (primary antibody) followed by staining with PE-conjugated secondary antibody using flow cytometry. The double positive cells for anti-GXM and CAR-GFP demonstrated the interaction between GXMR-CAR$^+$ T cells and GXM from *Cryptococcus* sp. Normal T cells and CAR T cells not incubated with *Cryptococcus* sp. polysaccharide antigens (no GXM) were used for dot plot calibration.

The ability of GXMR-CAR-T cells and Normal T cells to recognize GXM from Cryptococcus sp. was determined by incubation with C. neoformans polysaccharide antigens. Human T cells transduced with GXMR-CAR viral particles and Normal cells (mock transduced cells) were incubated with a preparation of Cryptococcus sp. polysaccharide antigens at 1:100 dilution. After 24 h, images were acquired by bright-field microscopy at 400× magnification (FIG. 7A). The positive control used IMMUNOCULT™ Human CD3/CD28 T cell activator to induce the activation of human T cells by following the manufacture's instructions (StemCell Technologies). For a negative control, the cells incubated with medium alone.

Figure 7B:
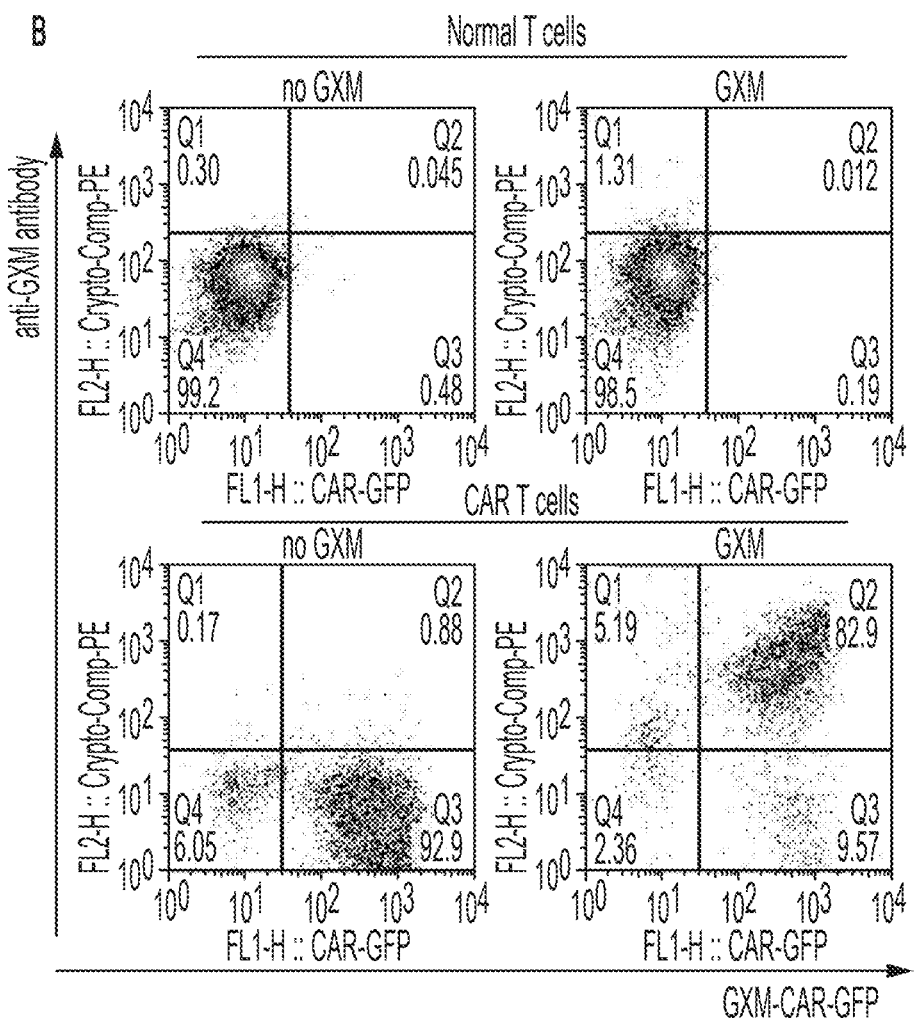

GXMR-CAR-T cells and Normal T cells incubated with Cryptococcus sp. polysaccharide antigens at 1:100 dilution. After washing with PBS, GXM was detected on cell surface by flow cytometry after incubation with a mouse anti-GXM monoclonal antibody (EMD Millipore Corporation, cat. #MABF2069) and goat anti-mouse IgG PE-conjugated secondary antibody (Jackson Immunoresearch Laboratories Inc.; Cat. No. 115-116-071). GXMR-CAR T cells that were identified by both GFP expression (x-axis) and anti-GXM antibody binding (y-axis) were considered to be able to bind to GXM (FIG. 7B).

Figure 8:
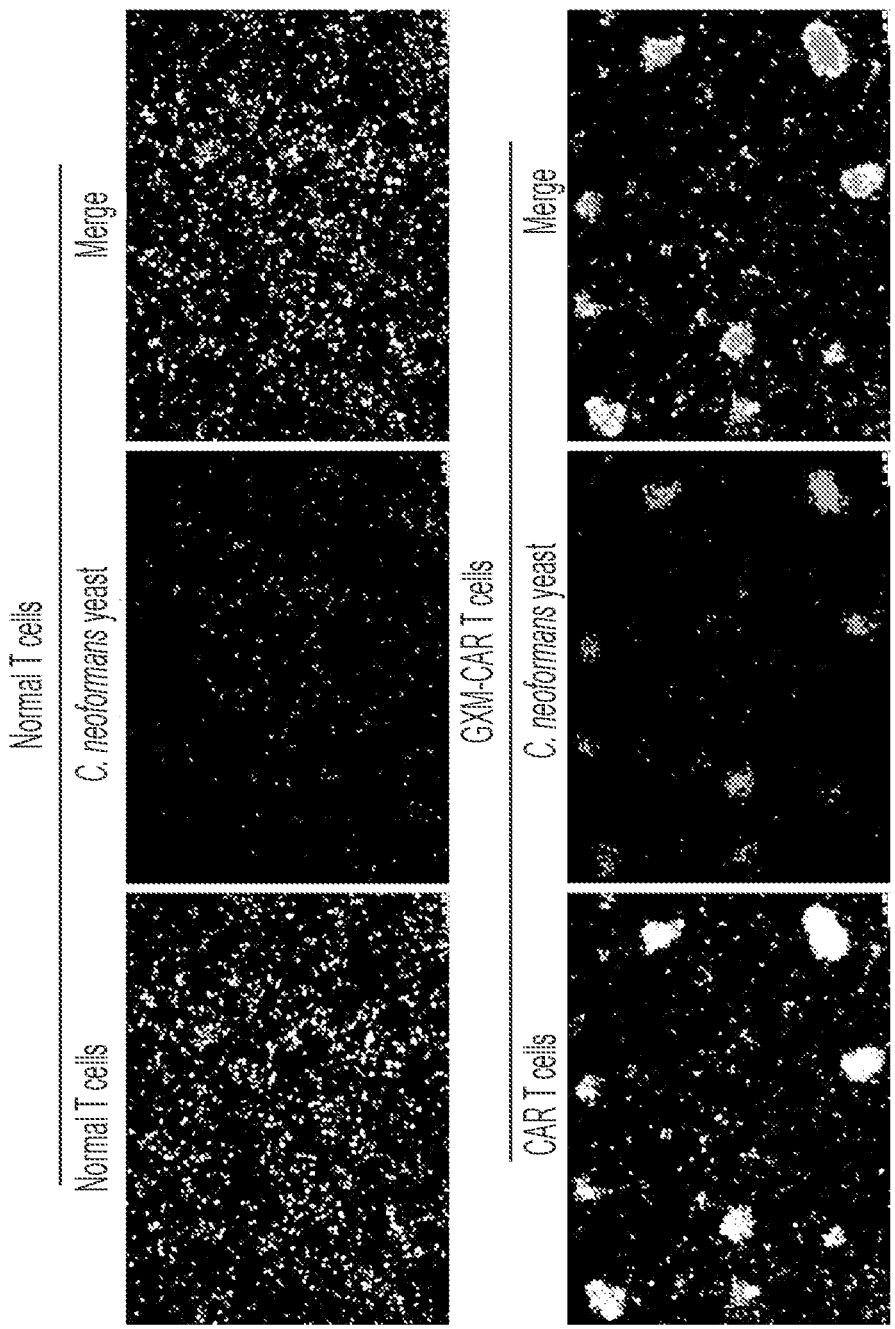
FIG. 8: Immunofluorescence assay demonstrates the recognition of *C. neoformans* yeast by GXMR-CAR$^+$ T cells. Human T cells transduced with GXMR-CAR lentiviral particles or mock transduced cells (negative control; Normal T cells labeled with CFSE) were incubated with *C. neoformans* yeast labeled with calcofluor-white. The interaction between GXMR-CAR$^+$ T cells or normal T cells with *C. neoformans* was evaluated by fluorescence microscopy. The image on the right displays the co-localization of GXMR-CAR$^+$ cells or Normal T cells and *C. neoformans* yeast.

Fluorescence microscopy was used to visualize the interaction between GXMR-CAR T cells (GFP positive) and C. neoformans yeast. The C. neoformans yeast was labeled with calcofluor-white (Thermo Fischer Scientific, Cat. No. L7009), according to the manufacturer's instructions. GXMR-CAR T and Normal T cells (mock transduced cells) were labeled with CFSE, cultured at a concentration of 1×10$^6$ cells/mL, and incubated with yeast (1×10$^5$ cells/mL) at 37° C. After 24 h, the interaction between GXMR-CAR T cells or normal T cells and C. neoformans (blue) was detected by fluorescence microscopy at 100× magnification. This study shows that the GXMR-CAR specifically targets Glucuronoxylomannan (GXM) a polysaccharide located in the capsule of Cryptococcus sp. In addition, the GXM is the major virulence factor in Cryptococcus sp. (FIG. 8).

Figure 9:
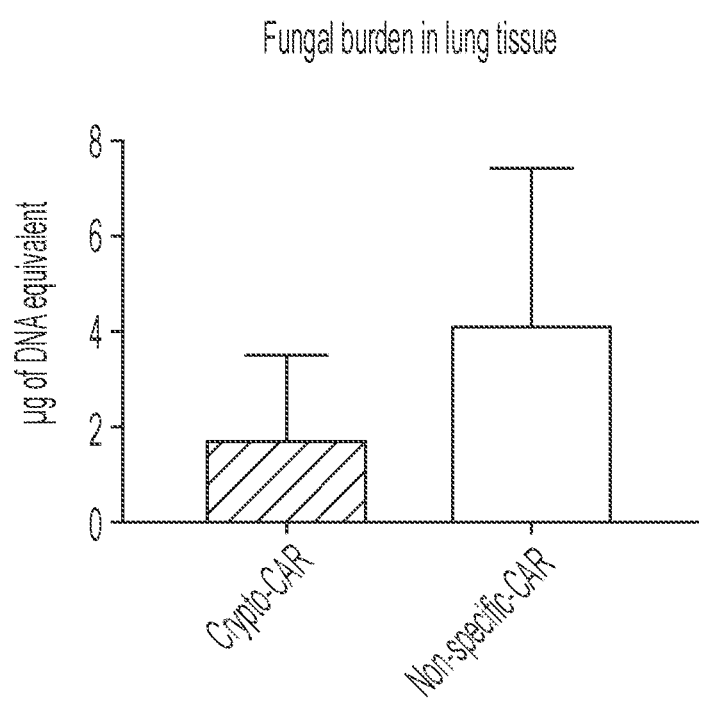
FIG. 9: Measurement of fungal burden by qPCR to evaluate the targeting efficacy of GXMR-CAR$^+$ T cells in a pulmonary *Cryptococcus* model.

In vivo therapeutic studies were performed in the animal model bearing ycurptococcus infection. NSG mice were used for these studies because they are deficient in mature B, T, and NK cells, therefore they are unable to target and destroy the infused GXMR-CAR T cells. Pulmonary fungal infection was established by infecting the lungs with *C. neoformans* yeast ($1 \times 10^5$ yeast per mouse) via intranasal infusion (Angkasekwinai et al., 2014). 1 and 3 days post-infection the mice were treated with GXMR-CAR T cells, NS-CAR T cells, or PBS, and on day 8 post-infection the mice were humanely euthanized, and lung tissues were isolated to measure fungal burden by qPCR. A reduction of *C. neoformans* from lungs of the GXMR-CAR treated mice compared to NSG mice that received non-specific CAR T cells. Genomic DNA was isolated from lung tissue homogenates using Qiagen genomic DNA spin column kit following manufacturer's instructions. 100 ng of gDNA was used to perform real-time quantitative polymerase chain (qPCR) analysis. *Cryptococcus* primers and the TAQMAN® probe were designed according to a published study (Veron et al., 2009), CneoFwd 5'-GCCGCGACCTGCAAAG-3' (SEQ ID NO: 10), CneoRev 5'-GGTAATCACCTTCC-CACTAACACAT-3' (SEQ ID NO: 11), CneoProbe 5'-FAMACGTCGGCTCGCC-MGB-3' (SEQ ID NO: 12) (MGB: Minor Groove Binder; Applied Biosystems), located in the ITS2-rDNA region. The reduction of *Cryptococcus* was confirmed from lungs of the GXMR-CAR treated mice. NSG mice that received non-specific CAR T cells (NS-CAR) served as negative control. Overall, the GXMR-CAR-treated group had a lower fungal burden in the lungs compared with the NS-CAR group (FIG. 9).

Figure 10:
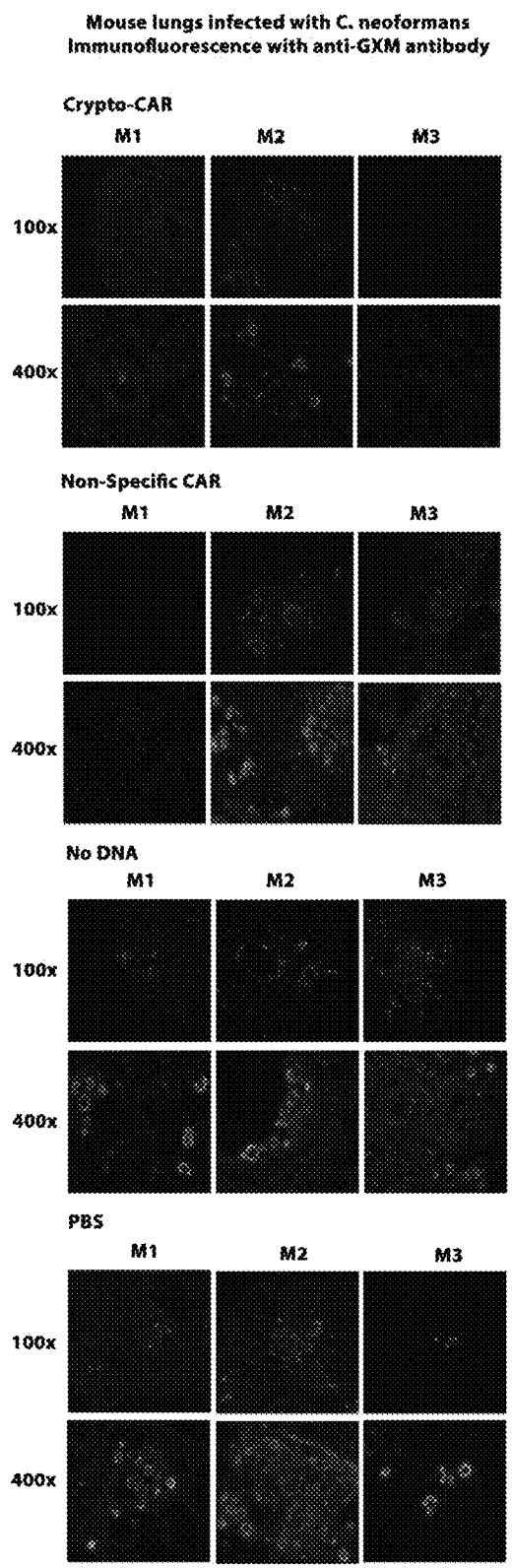
FIG. 10: Immunofluorescence assay detects GXM positive Titan cells in *Cryptococcus* treated mouse lungs.

The lungs of NSG mice were infected with *C. neoformans* yeast ($1 \times 10^5$ per mouse) via intranasal infusion. 1 and 3 days post-infection the mice were treated with GXMR-CAR T cells, NS-CAR T cells, or PBS, and on day 8 post-infection the mice were humanely euthanized. A study was performed with lung tissue sections from PBS, GXMR-CAR, NS-CAR$^+$ T cells, and NoDNA (mock transfected cell) treated mice. Paraffin sections were deparaffinized, antigen retrieval was performed with sodium citrate buffer, then samples were treated with BLOCKAID™ (Thermo), incubated with anti-GXM, (cat. #MABF2069, EMD Millipore, 1:100 dilution), washed, incubated with anti-Mouse IgG1-FITC, (cat. #5534431, BD Pharmingen, 1:100 dilution), washed, and imaged using Nikon Eclipse Ti microscope. Reduced size and number of stained Titan cells (Hallmark of *Cryptococcus* infection) was observed in the GXMR-CAR samples compared to the negative controls, indicating a reduced fungal burden due to GXMR-CAR. Corroborating the in vitro results, these data indicate that GXMR-CAR$^+$ T cells can decrease fungal growth in vivo by directly targeting fungal hyphae (FIG. 10).

Figure 11:
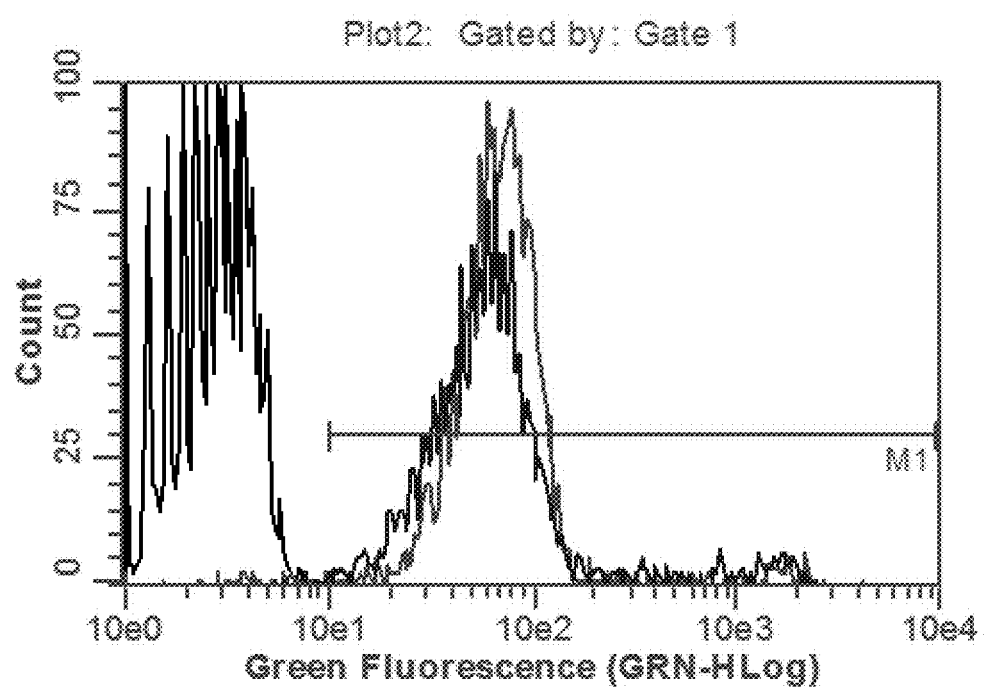
FIG. 11: FITC-conjugated anti-GXM antibody targets both live *Cryptococcus* and heat killed form of *Cryptococcus* in the same manner. Both the curves overlap each other. Anti-mouse IgG-FITC (left) served as a negative control.

Anti-GXM antibody 18B7 targets both live *Cryptococcus* and heat killed *Cryptococcus* with the same intensity: Cells from *C. neoformans* strain H99 (ATCC cat #32045) were incubated with PBS/10% fetal bovine serum for 20 min at 4° C. to inhibit nonspecific antibody binding. To produce heat killed *C. neoformans*, H99 cells ($1 \times 10^6$ cells/ml) were washed and incubated at 70° C. for 1 h to inactive the H99 cells. In contrast, live cells were washed but not heat inactivated. The live and heat-killed cells were washed twice with PBS and the anti-GXM antibody (18B7 clone; 1:100; Cat #MABF2069 EMD Millipore Corporation) was added; after 45 min of incubation, these cells were washed with PBS and incubated with anti-mouse IgG-FITC antibody (1:100; Sigma-Aldrich) for 40 min at 4° C. The live cells incubated with anti-mouse IgG-FITC antibody alone (1:100; Sigma-Aldrich) were considered as Isotype controls. The ability of anti-GXM to bind to H99 cells was determined by flow cytometry (Guava easyCyte, Guava Technologies, Millipore, Hayward, CA, USA). The M1 marker in the histogram represents the field of positive cells recognized by anti-GXM antibody. The results of flow cytometry suggest that the GXM-CAR has the ability to target live *Cryptococcus* in the same manner it targets the heat killed form of *Cryptococcus* (FIG. 11).

Figures 12D, 12E:
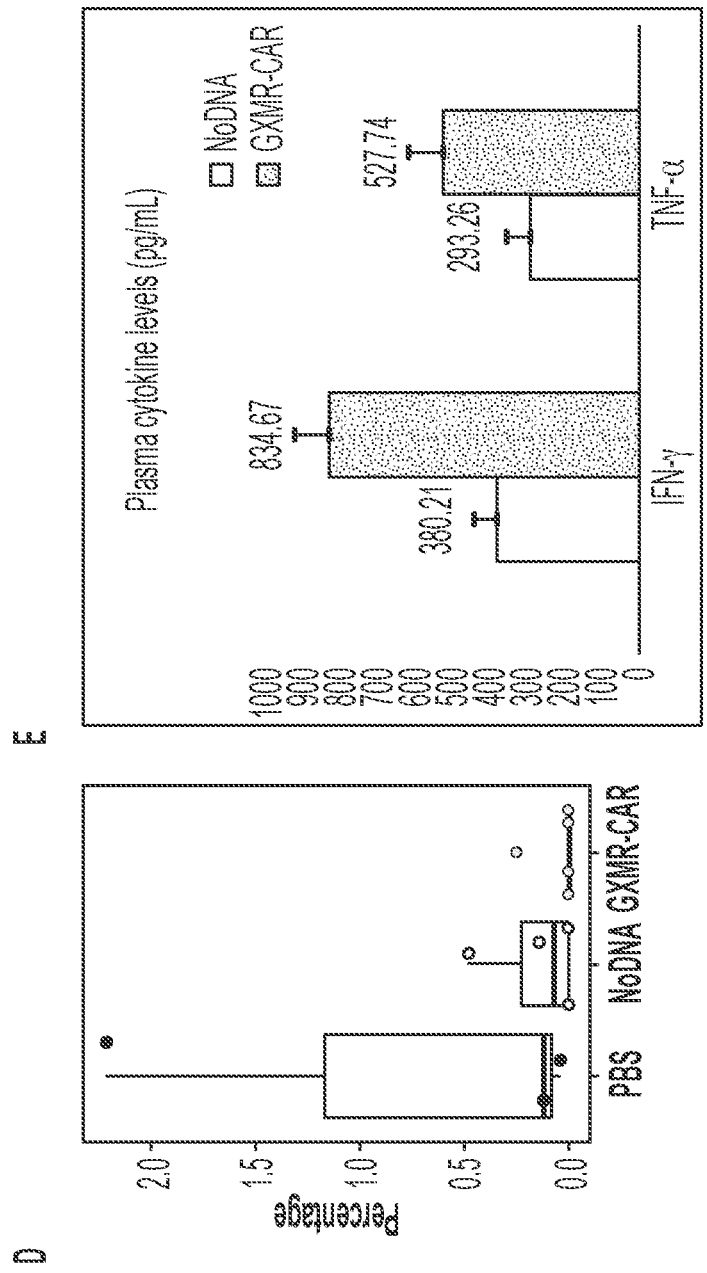

Quantitation of *C. neoformans* Titan cells in lung tissue: NOD Scid gamma (NSG) mice were used for these studies because they are deficient in mature B, T, and natural killer cells. Therefore, they are unable to target and destroy infused GXMR-CAR$^+$ T cells. Pulmonary fungal infection was established in the mice by infecting their lungs with *C. neoformans* yeast ($1 \times 10^5$/mouse) via intranasal infusion. The mice were placed into 3 groups according to the infusions they received: GXMR-CAR$^+$ T cells, NoDNA T cells, and phosphate-buffered saline (PBS). The mice were infused with 5 million GXMR-CAR$^+$ T cells, NoDNA T cells, or PBS alone via tail vein injection at 1 and 4 days after infection. Eight days after infection, the mice were humanely euthanized and entire sections of lung tissue were evaluated by immunofluorescence using an anti-GXM antibody and imaging was performed at 400× (FIG. 12A). More than 2000 images were analyzed using the automated INFORM® Cell Analysis™ software to quantify the area of GXM-FITC stained Titan cells (FIG. 12B) and total area of lung tissue on each slide. A smaller area of GXM positive Titan cells (hallmark of *Cryptococcus* infection in the lung) was observed in the GXMR-CAR samples (0.021 mm$^2$ GXM, 57.55 mm$^2$ lung) compared to the negative controls (PBS: 0.37 mm$^2$ GXM, 39.2 mm$^2$ lung; NoDNA: 0.066 mm$^2$ GXM, 60.0 mm$^2$ lung), indicating a reduced fungal burden due to treatment with GXMR-CAR$^+$ T cells. These results were supported by Gomori methenamine-silver (GMS) staining of Titan cells in lung tissue sections obtained from the mice in the PBS, GXMR-CAR$^+$ T-cell, and NoDNA T-cell groups. A lower fungal burden was observed in the GXMR-CAR$^+$ T-cell group compared with the PBS group. Activated CAR T-cell secretes human cytokines in plasma which was measured using Bio-Plex Pro Human Cytokine 27-Plex Immunoassay (Bio-Rad, Hercules, CA, USA, catalog #M500KCAF0Y) on a Bio-Plex-200 according to the manufacturers' instructions. Plasma cytokines were measured on the 8$^{th}$ day and the Pro-inflammatory cytokines such as IFN-γ and TNF-α slightly increased in the plasma of CAR T-cell treated group when compared to NoDNA treated group suggests for in vivo CAR T-cell activation.

Figure 13A:
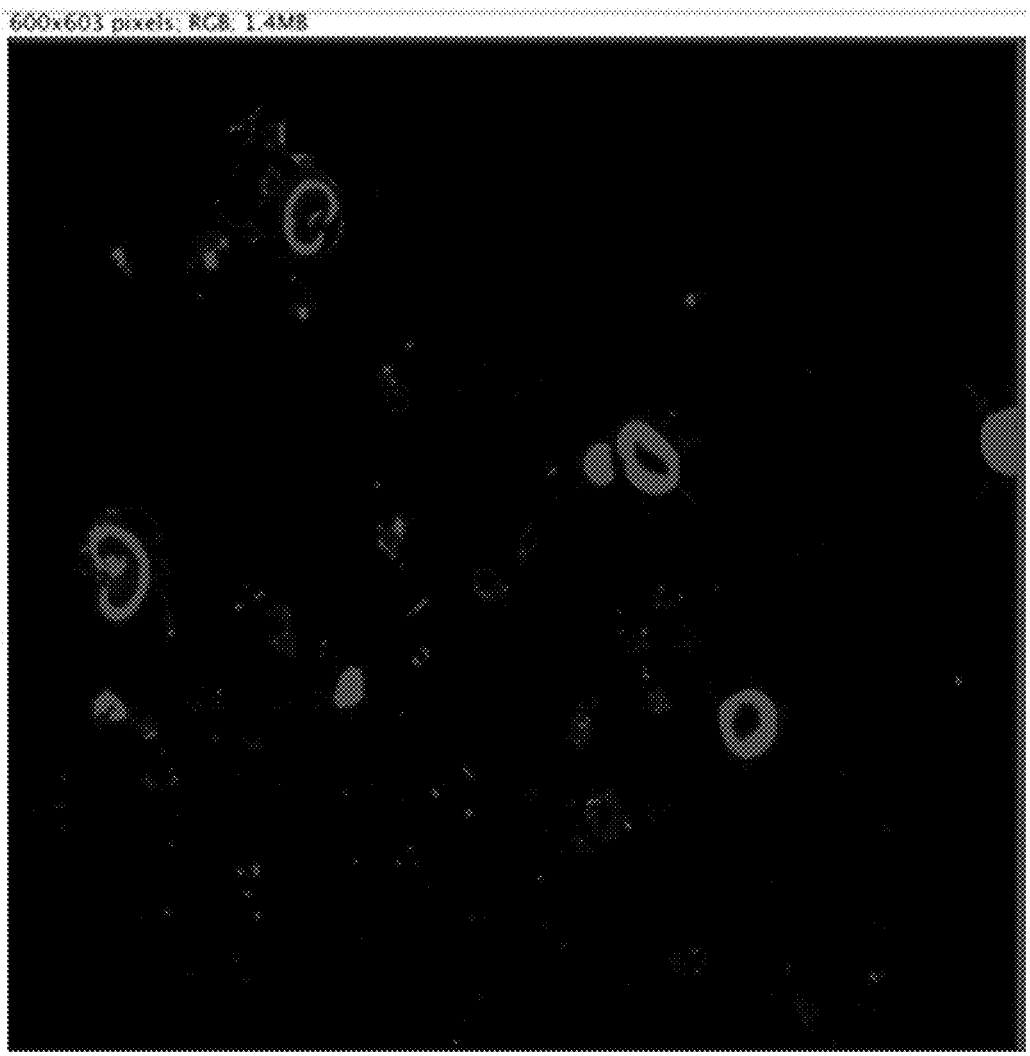
FIGS. 13A-13B: ImageJ analysis of anti-GXM immunofluorescence assay shows reduced area of GXM positive Titan cells in the lungs of *C. neoformans* infected mice treated with GXMR-CAR+ T cells. The lungs of NSG mice (5 per group) were infected with *C. neoformans* yeast ($1\times10^5$/mouse) via intranasal infusion. Mice were infused intravenously with 5 million GXMR-CAR+ T cells, NoDNA T cells or PBS alone on days 1 and 4 after infection. Eight days after infection, the mice were humanely euthanized. (A) Paraffin-embedded lung tissue sections from the mice were incubated with an anti-GXM antibody and anti-mouse-FITC secondary to detect Titan cells. Images were acquired at 200× magnification using an Olympus CKX41 microscope. GXM-FITC labeled Titan cells are shown. (B) ImageJ software was used to quantify the area of GXM positive staining in lungs from the nine the images that are shown in FIG. 10. A statistically significant reduction in the area of GXM stained Titan cells was demonstrated in GXMR-CAR T cell treated mice compared with PBS controls.
Figure 13B:
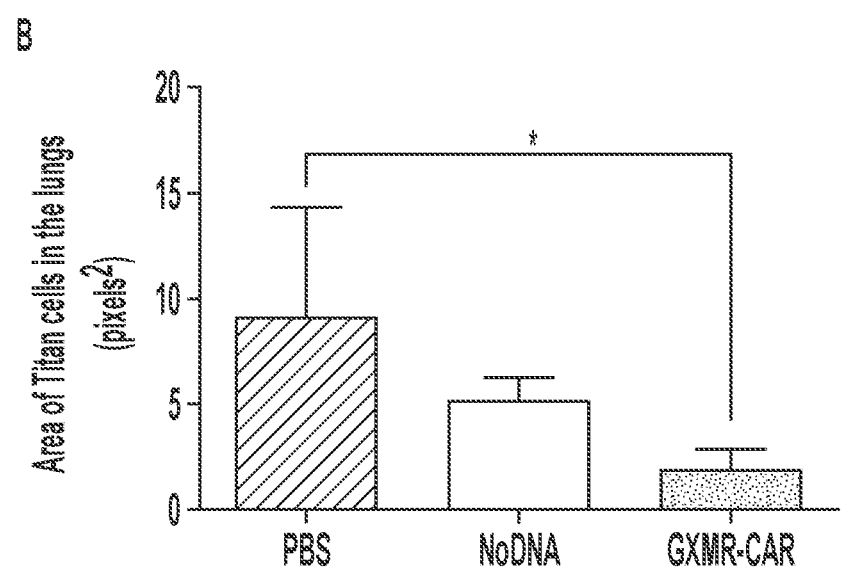

In addition, ImageJ was used to analyze the nine anti-GXM immunofluorescence images shown in FIG. 13A, and determine the area of GXM positive staining in the lung tissues. The ImageJ analysis demonstrated a significant reduction in the area of GXM staining in the GXMR-CAR T cell treated group compared to the PBS control. Corroborating the in vitro results, these data demonstrate that intravenously infused GXMR-CAR$^+$ T cells directly target *C. neoformans* and control its spread in the lungs of infected mice.

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Angkasekwinai et al., *Infect Immun.* 2014; 82 (9): 3880-90.

Ausubel et al., *Current Protocols in Molecular Biology*, Greene Publishing Associates and John Wiley & Sons, NY, 1994.

International Patent Publication No. WO2014/055668

Remington's Pharmaceutical Sciences 22$^{nd}$ edition, 2012.

Sambrook et al., *Molecular Cloning: A Laboratory Manual*, 3$^{rd}$ ed., Cold Spring Harbor Press, Cold Spring Harbor, N.Y. 2001.

Veron et al., *Diagnos Microbio Infect Dis*, 2009.

What is claimed is:

1. A chimeric antigen receptor (CAR) comprising (a) a glucuronoxylomannan (GXM) scFv comprising an amino acid sequence of SEQ ID NO: 2, (b) signaling domains CD3ξ, CD28, OX40/CD134, 4-1BB/CD137, TRAM, MyD88, TRAF 6, pattern recognition receptor family member, Toll-like-receptor (TLR) family member or a combination thereof, and (c) a CD28, CD8α, CD134, CD137, pattern recognition receptor (PRR) or TLR transmembrane domain.

2. The CAR of claim 1, wherein the scFv is encoded by a nucleotide sequence of SEQ ID NO:1.

3. The CAR of claim 1, wherein the CAR comprises the GXM scFv, IgG4-M spacer, CD28 transmembrane domain, CD28 signaling domain, and CD3ξ signaling domain.

4. The CAR of claim 3, wherein the CAR is encoded by a nucleotide sequence with at least 95% sequence identity to SEQ ID NO:3.

5. The CAR of claim 3, wherein the CAR is encoded by a nucleotide sequence of SEQ ID NO:3.

6. An isolated polynucleotide encoding the CAR of claim 1.

7. The isolated polynucleotide of claim 6, wherein the polynucleotide comprises SEQ ID NO:3.

8. An expression vector encoding the CAR of claim 1.

9. An immune cell engineered to express the CAR comprising a GXM antigen-binding domain according to claim 1.

10. A pharmaceutical composition comprising a population of cells according to claim 9.

11. A method of treating a fungal infection in a subject comprising administering an effective amount of cells of claim 9 to the subject.

12. The method of claim 11, wherein the fungal infection is an invasive fungal infection.

13. The method of claim 12, wherein the invasive fungal infection is drug resistant.

* * * * *